(12) United States Patent
Eastwood

(10) Patent No.: US 6,620,832 B2
(45) Date of Patent: Sep. 16, 2003

(54) SUBSTITUTED UREAS

(75) Inventor: Paul Robert Eastwood, Romford (GB)

(73) Assignee: Aventis Pharma Ltd., Kent (GB)

( * ) Notice: Subject to any disclaimer, the term of this patent is extended or adjusted under 35 U.S.C. 154(b) by 0 days.

(21) Appl. No.: 10/002,747

(22) Filed: Nov. 2, 2001

(65) Prior Publication Data

US 2002/0082255 A1 Jun. 27, 2002

Related U.S. Application Data

(63) Continuation of application No. PCT/GB00/01734, filed on May 5, 2000.
(60) Provisional application No. 60/152,855, filed on Sep. 8, 1999, provisional application No. 60/152,861, filed on Sep. 8, 1999, and provisional application No. 60/152,860, filed on Sep. 8, 1999.

(30) Foreign Application Priority Data

May 5, 1999 (GB) ............................................. 9910396
May 5, 1999 (GB) ............................................. 9910405
May 5, 1999 (GB) ............................................. 9910417

(51) Int. Cl.$^7$ ........................ A61K 31/40; C07D 209/08
(52) U.S. Cl. ........................ 514/378; 514/415; 548/248; 548/491
(58) Field of Search ................................. 548/491, 248; 514/378, 415

(56) References Cited

U.S. PATENT DOCUMENTS 5,212,320 A * 5/1993 Okada et al. ................ 514/415
5,849,764 A 12/1998 Goulet et al.

FOREIGN PATENT DOCUMENTS

| WO | WO 99/10312 | 3/1999 |
| WO | WO 99/20272 | 4/1999 |
| WO | WO 00/43651 | 9/1999 |
| WO | WO 00/15612 | 3/2000 |
| WO | WO 00/39103 | 7/2000 |

* cited by examiner

Primary Examiner—Laura L. Stockton
(74) Attorney, Agent, or Firm—Ronald G. Ort

(57) ABSTRACT

The invention is directed to physiologically active compounds of general formula (I):

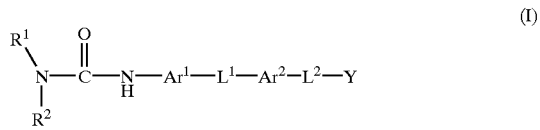

wherein $R^1$ is lower alkyl, $R^2$ is aryl, arylalkyl, heteroaryl or heteroarylalkyl, or $R^1$ and $R^2$ together with the nitrogen atom to which they are attached form a cyclic amine, $Ar^1$ is aryldiyl or heteroaryldiyl, $Ar^2$ is optionally substituted phenylene or heteroaryldiyl, $L^1$ is an a —$R^5$—$R^6$— linkage where $R^5$ is alkylene, alkenylene or alkynylene and $R^6$ is a direct bond, cycloalkylene, heterocycloalkylene, arylene, heteroaryldiyl, —C(=$Z^1$)—$NR^4$—, —$NR^4$—C(=$Z^1$)—, —$Z^1$—, —C(=O)—, —C(=$NOR^4$)—, —$NR^4$—, —$NR^4$—C(=$Z^1$)—$NR^4$—, —$SO_2$—$NR^4$—, —$NR^4$—$SO_2$—, —O—C(=O)—, —C(=O)—O—, —$NR^4$—C(=O)—O— or —O—C(=O)—$NR^4$—, $L^2$ is a direct bond, an optionally substituted alkylene, alkenylene, alkynylene, cycloalkenylene, cycloalkylene, heteroaryldiyl, heterocycloalkylene or aryldiyl linkage, a —[C(=O)—N($R^9$)—C($R^4$)($R^{10}$)]$_p$— linkage, a —$Z^3$—$R^{11}$— linkage, a —C(=O)—$CH_2$—C(=O)— linkage or a —$R^{11}$—$Z^3$—$R^{11}$— linkage, and Y is carboxy or an acid bioisostere; and the corresponding N-oxides, and their prodrugs; and pharmaceutically acceptable salts and solvates (e.g. hydrates) of such compounds and their N-oxides and prodrugs.

Such compounds have valuable pharmaceutical properties, in particular the ability to regulate the interaction of VCAM-1 and fibronectin with the integrin VLA-4 (α4β1).

27 Claims, No Drawings

SUBSTITUTED UREAS

This application is a continuation of PCT/GB00/01734, filed May 5, 2000, which claims priority from GB Application Nos. 9910417.6, 9910405.1, and 9910396.2, all filed May 5, 1999, and U.S. Provisional Application Nos. 60/152,855, 60/152,861, and 60/152,860, all filed Sep. 8, 1999; all these applications incorporated herein by reference.

This invention is directed to ureas, their preparation, pharmaceutical compositions containing these compounds, and their pharmaceutical use in the treatment of disease states capable of being modulated by the inhibition of cell adhesion.

Cell adhesion is a process by which cells associate with each other, migrate towards a specific target or localise within the extra-cellular matrix. Many of the cell—cell and cell-extracellular matrix interactions are mediated by protein ligands (e.g. fibronectin, VCAM-1 and vitronectin) and their integrin receptors [e.g. $\alpha5\beta1$ (VLA-5), $\alpha4\beta1$ (VLA-4) and $\alpha V\beta3$]. Recent studies have shown these interactions to play an important part in many physiological (e.g. embryonic development and wound healing) and pathological conditions (e.g. tumour-cell invasion and metastasis, inflammation, atherosclerosis and autoimmune disease).

A wide variety of proteins serve as ligands for integrin receptors. In general, the proteins recognised by integrins fall into one of three classes: extracellular matrix proteins, plasma proteins and cell surface proteins. Extracellular matrix proteins such as collagen fibronectin, fibrinogen, laminin, thrombospondin and vitronectin bind to a number of integrins. Many of the adhesive proteins also circulate in plasma and bind to activated blood cells. Additional components in plasma that are ligands for integrins include fibrinogen and factor X. Cell bound complement C3bi and several transmembrane proteins, such as Ig-like cell adhesion molecule (ICAM-1,2,3) and vascular cell adhesion molecule (VCAM-1), which are members of the Ig superfamily, also serve as cell-surface ligands for some integrins.

Integrins are heterodimeric cell surface receptors consisting of two subunits called $\alpha$ and $\beta$. There are at least fifteen different $\alpha$-subunits ($\alpha1$-$\alpha9$, $\alpha$-L, $\alpha$-M, $\alpha$-X, $\alpha$-IIb, $\alpha$-V and $\alpha$-E) and at least seven different $\beta$ ($\beta1$-$\beta7$) subunits. The integrin family can be subdivided into classes based on the $\beta$ subunits, which can be associated with one or more $\alpha$-subunits. The most widely distributed integrins belong to the $\beta1$ class, also known as the very late antigens (VLA). The second class of integrins are leukocyte specific receptors and consist of one of three $\alpha$-subunits ($\alpha$-L, $\alpha$-M or $\alpha$-X) complexed with the $\beta2$ protein. The cytoadhesins $\alpha$-IIb$\beta3$ and $\alpha$-V$\beta3$, constitute the third class of integrins.

The present invention principally relates to agents which modulate the interaction of the ligand VCAM-1 with its integrin receptor $\alpha4\beta1$ (VLA-4), which is expressed on numerous hematopoietic cells and established cell lines, including hematopoietic precursors, peripheral and cytotoxic T lymphocytes, B lymphocytes, monocytes, thymocytes and eosinophils.

The integrin $\alpha4\beta1$ mediates both cell—cell and cell-matrix interactions. Cells expressing $\alpha4\beta1$ bind to the carboxy-terminal cell binding domain (CS-1) of the extracellular matrix protein fibronectin, to the cytokine-inducible endothelial cell surface protein VCAM-1, and to each other to promote homotypic aggregation. The expression of VCAM-1 by endothelial cells is upregulated by proinflammatory cytokines such as INF-$\gamma$, TNF-$\alpha$, IL-1$\beta$ and IL-4.

Regulation of $\alpha4\beta1$ mediated cell adhesion is important in numerous physiological processes, including T-cell proliferation, B-cell localisation to germinal centres, and adhesion of activated T-cells and eosinophils to endothelial cells. Evidence for the involvement of VLA-4/VCAM-1 interaction in various disease processes such as melanoma cell division in metastasis, T-cell infiltration of synovial membranes in rheumatoid arthritis, autoimmune diabetes, collitis and leukocyte penetration of the blood-brain barrier in experimental autoimmune encephalomyelitis, atherosclerosis, peripheral vascular disease, cardiovascular disease and multiple sclerosis, has been accumulated by investigating the role of the peptide CS-1 (the variable region of fibronectin to which $\alpha4\beta1$ binds via the sequence Leu-Asp-Val) and antibodies specific for VLA-4 or VCAM-1 in various in vitro and in vivo experimental models of inflammation. For example, in a Streptococcal cell wall-induced experimental model of arthritis in rats, intravenous administration of CS-1 at the initiation of arthritis suppresses both acute and chronic inflammation (S. M. Wahl et al., J.Clin.Invest., 1994, 94, pages 655–662). In the oxazalone-sensitised model of inflammation (contact hypersensitivity response) in mice, intravenous administration of anti-$\alpha4$ specific monoclonal antibodies significantly inhibited (50–60% reduction in the ear swelling response) the efferent response (P. L. Chisholm et al. J.Immunol., 1993, 23, pages 682–688). In a sheep model of allergic bronchoconstriction, HP1/2, an anti-$\alpha4$ monoclonal antibody given intravenously or by aerosol, blocked the late response and the development of airway hyperresponsiveness (W. M. Abraham et al. J. Clin. Invest., 1994, 93 pages 776–787).

We have now found a novel group of ureas which have valuable pharmaceutical properties, in particular the ability to regulate the interaction of VCAM-1 and fibronectin with the integrin VLA-4 ($\alpha4\beta1$).

Thus, in one aspect, the present invention is directed to compounds of general formula (I)

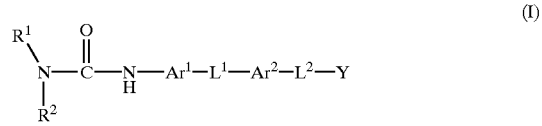

wherein:

$R^1$ represents lower alkyl;

$R^2$ represents aryl, arylalkyl, heteroaryl or heteroarylalkyl; or $R^1$ and $R^2$ together with the nitrogen atom to which they are attached form a cyclic amine;

$R^3$ represents alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^4$ represents hydrogen or lower alkyl;

$R^5$ is an alkylene chain, an alkenylene chain or an alkynylene chain;

$R^6$ is a direct bond, cycloalkylene, heterocycloalkylene, aryldiyl, heteroaryldiyl, —C(=Z$^1$)—NR$^4$—, —NR$^4$—C(=Z$^1$)—, —Z$^1$—, —C(=O)—, —C(=NOR$^4$)—, —NR$^4$—, —NR$^4$—C(=Z$^1$)—NR$^4$—, —SO$_2$—NR$^4$—, —NR$^4$—SO$_2$—, —O—C(=O)—, —C(=O)—O—, —NR$^4$—C(=O)—O— or —O—C(=O)—NR$^4$—;

$R^7$ is hydrogen, alkyl, aryl, arylalkyl, cycloalkyl, cycloalkylalkyl, heteroaryl, heteroarylalkyl, heterocycloalkyl or heterocycloalkylalkyl;

$R^8$ is alkyl, aryl, cycloalkyl, heteroaryl or heterocycloalkyl, or alkyl substituted by aryl, an acidic functional group, cycloalkyl, heteroaryl, heterocycloalkyl, $-Z^1H$, $-Z^2R^3$, $-C(=O)-NY^1Y^2$ or $-NY^1Y^2$;

$R^9$ is hydrogen, $R^3$ or alkyl substituted with alkoxy, cycloalkyl, hydroxy, mercapto, alkylthio or $-NY^1Y^2$;

$R^{10}$ is hydrogen or a group consisting amino acid side chains, an acidic functional group, $R^3$, $-Z^2R^3$, $-C(=O)-R^3$, or $-C(=O)-NY^1Y^2$, or alkyl substituted by an acidic functional group or by $R^3$, $-Z^2R^3$, $-NY^1Y^2$, $-NH-C(=O)-R^3-C(=O)-R^5-NH_2$, $-C(=O)-Ar^3-NH_2$, $-C(=O)-R^5-CO_2H$, or $-C(=O)-NY^1Y^1$;

or $R^9$ and $R^{10}$ together with the atoms to which they attached form a 3- to 6-membered heterocycloalkyl ring;

$R^{11}$ is $C_{1-6}$alkylene, optionally substituted by $R^3$;

$R^{12}$ is hydrogen, or alkyl optionally substituted by aryl, an acidic functional group, cycloalkyl, heteroaryl, heterocycloalkyl, $-Z^1H$, $-Z^2R^3$, $-C(=O)-NY^1Y^2$ or $-NY^1Y^2$;

$Ar^1$ is aryldiyl or heteroaryldiyl;

$Ar^2$ is heteroaryldiyl, phenylene or phenylene substituted by halogen, lower alkyl or lower alkoxy;

$Ar^3$ is aryldiyl or heteroaryldiyl;

$L^1$ represents a $-R^5-R^6-$ linkage;

$L^2$ represents:

(i) a direct bond;

(ii) an alkylene, alkenylene, alkynylene, cycloalkenylene, cycloalkylene, heteroaryldiyl, heterocycloalkylene or aryldiyl linkage each optionally substituted by (a) an acidic functional group, $R^3$, $-Z^1H$, $-Z^2R^8$, $-C(=O)-R^3$, $-N(R^7)-C(=O)-R^8$, $-N(R^7)-C(=O)-OR^8$, $-N(R^7)-C(=O)-NR^4R^8$, $-N(R^7)-SO_2-R^8$, $-NY^1Y^2$, or $-[C(=O)-N(R^9)-C(R^4)(R^{10})]_p-C(=O)-NY^1Y^2$, or by (b) alkyl substituted by an acidic functional group, or by $-Z^1H$, $-Z^2R^3$, $-C(=O)-NY^1Y^2$ or $-NY^1Y^2$;

(iii) a $-[C(=O)-N(R^9)-C(R^4)(R^{10})]_p-$ linkage;

(iv) a $-Z^3-R^{11}-$ linkage;

(v) a $-C(=O)-CH_2-C(=O)-$ linkage; or (vi) a $-R^{11}-Z^3-R^{11}-$ linkage;

Y is carboxy or an acid bioisostere;

$Y^1$ and $Y^2$ are independently hydrogen, alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, $-NY^3Y^4$, or one or more $-CO_2R^7$ or $-C(=O)-NY^3Y^4$ groups; or the group $-NY^1Y^2$ may form a cyclic amine;

$Y^3$ and $Y^4$ are independently hydrogen, alkenyl, alkyl, aryl, arylalkyl, cycloalkyl, heteroaryl or heteroarylalkyl; or the group $-NY^3Y^4$ may form a cyclic amine;

$Z^1$ is O or S;

$Z^2$ is O or $S(O)_n$;

$Z^3$ is O, $S(O)_n$, $NR^{12}$, $SO_2NR^{12}$, $NR^{12}C(=O)$, $C(=O)NR^{12}$ or $C(=O)$; and n is zero or an integer 1 or 2;

p is zero or an integer 1 to 4;

(but excluding compounds where an oxygen, nitrogen or sulphur atom is attached directly to a carbon carbon multiple bond of an alkenyl or alkynyl residue);

and the corresponding N-oxides, and their prodrugs; and pharmaceutically acceptable salts and solvates (e.g. hydrates) of such compounds and their N-oxides and prodrugs.

In the present specification, the term "compounds of the invention", and equivalent expressions, are meant to embrace compounds of general formula (I) as hereinbefore described, which expression includes the prodrugs, protected derivatives of compounds of formula (I) containing one or more acidic functional groups and/or amino-acid side chains, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

As used above, and throughout the description of the invention, the following terms, unless otherwise indicated, shall be understood to have the following meanings:

"Patient" includes both human and other mammals.

"Acid bioisostere" means a group which has chemical and physical similarities producing broadly similar biological properties to a carboxy group (see Lipinski, Annual Reports in Medicinal Chemistry, 1986,21,p283 "Bioisosterism In Drug Design"; Yun, Hwahak Sekye, 1993,33,p576–579 "Application Of Bioisosterism To New Drug Design"; Zhao, Huaxue Tongbao, 1995,p34–38 "Bioisosteric Replacement And Development Of Lead Compounds In Drug Design"; Graham, Theochem, 1995,343,p105–109 "Theoretical Studies Applied To Drug Design:ab initio Electronic Distributions In Bioisosteres"). Examples of suitable acid bioisosteres include: $-C(=O)-NHOH$, $-C(=O)-CH_2OH$, $-C(=O)-CH_2SH$, $-C(=O)-NH-CN$, sulpho, phosphono, alkylsulphonylcarbamoyl, tetrazolyl, arylsulphonylcarbamoyl, heteroarylsulphonylcarbamoyl, N-methoxycarbamoyl, 3-hydroxy-3-cyclobutene-1,2-dione, 3,5-dioxo-1,2,4-oxadiazolidinyl or heterocyclic phenols such as 3-hydroxyisoxazolyl and 3-hydoxy-1-methylpyrazolyl.

"Acidic functional group" means a group with an acidic hydrogen within it. The "protected derivatives" are those where the acidic hydrogen atom has been replaced with a suitable protecting group. For suitable protecting groups see T. W. Greene and P. G. M. Wuts in "Protective Groups in Organic Chemistry" John Wiley and Sons, 1991. Exemplary acidic functional groups include carboxyl (and acid bioisosteres), hydroxy, mercapto and imidazole. Exemplary protected derivatives include esters of carboxy groups (i.e. $-CO_2R^{13}$ where $R^{13}$ is alkyl, aryl, arylalkyl, cycloalkyl, cycloalkylalkyl, heteroaryl, heteroarylalkyl, heterocycloalkyl or heterocycloalkylalkyl), ethers of hydroxy groups (i.e. $-OR^{13}$), thioethers of mercapto groups (i.e. $-SR^{13}$), and N-benzyl derivatives of imidazoles.

"Acyl" means an H—CO— or alkyl-CO— group in which the alkyl group is as described herein.

"Acylamino" is an acyl-NH— group wherein acyl is as defined herein.

"Alkenyl" means an aliphatic hydrocarbon group containing a carbon—carbon double bond and which may be straight or branched having about 2 to about 15 carbon atoms in the chain. Preferred alkenyl groups have 2 to about 12 carbon atoms in the chain; and more preferably 2 to about 6 carbon atoms (e.g. 2 to 4 carbon atoms) in the chain. "Branched", as used herein and throughout the text, means that one or more lower alkyl groups such as methyl, ethyl or propyl are attached to a linear chain; here a linear alkenyl chain. "Lower alkenyl" means about 2 to about 4 carbon atoms in the chain which may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl and decenyl.

"Alkenylene" means an aliphatic bivalent radical derived from a straight or branched alkenyl group, in which the alkenyl group is as described herein. Exemplary alkenylene radicals include vinylene and propylene.

"Alkoxy" means an alkyl-O— group in which the alkyl group is as described herein. Exemplary alkoxy groups include methoxy, ethoxy, n-propoxy, i-propoxy, n-butoxy and heptoxy.

"Alkoxyalkoxy" means an alkyl-O-alkyl-O— group wherein the alkyl groups independently are as defined above. Examples of alkoxyalkoxyl include methoxymethoxy, methoxyethoxy, ethoxyethoxy and the like.

"Alkoxycarbonyl" means an alkyl-O—CO— group in which the alkyl group is as described herein. Exemplary alkoxycarbonyl groups include methoxy- and ethoxycarbonyl.

"Alkyl" means, unless otherwise specified, an aliphatic hydrocarbon group which may be straight or branched having about 1 to about 15 carbon atoms in the chain optionally substituted by alkoxy or by one or more halogen atoms. Particular alkyl groups have from 1 to about 6 carbon atoms. "Lower alkyl" as a group or part of a lower alkoxy, lower alkylthio, lower alkylsulphinyl or lower alkylsulphonyl group means unless otherwise specified, an aliphatic hydrocarbon group which may be straight or branched having 1 to about 4 carbon atoms in the chain. Exemplary alkyl groups include methyl, ethyl, n-propyl, i-propyl, n-butyl, s-butyl, t-butyl, n-pentyl, 3-pentyl, heptyl, octyl, nonyl, decyl and dodecyl.

"Alkylene" means an aliphatic bivalent radical derived from a straight or branched alkyl group, in which the alkyl group is as described herein. Exemplary alkylene radicals include methylene, ethylene and trimethylene.

"Alkylenedioxy" means an —O-alkylene-O— group in which alkylene is as defined above. Exemplary alkylenedioxy groups include methylenedioxy and ethylenedioxy.

"Alkylsulphinyl" means an alkyl-SO— group in which the alkyl group is as previously described. Preferred alkylsulphinyl groups are those in which the alkyl group is $C_{1-4}$alkyl.

"Alkylsulphonyl" means an alkyl-$SO_2$— group in which the alkyl group is as previously described. Preferred alkylsulphonyl groups are those in which the alkyl group is $C_{1-4}$alkyl.

"Alkylsulphonylcarbamoyl" means an alkyl-$SO_2$—NH—C(=O)— group in which the alkyl group is as previously described. Preferred alkylsulphonylcarbamoyl groups are those in which the alkyl group is $C_{1-4}$alkyl.

"Alkylthio" means an alkyl-S— group in which the alkyl group is as previously described. Exemplary alkylthio groups include methylthio, ethylthio, isopropylthio and heptylthio.

"Alkynyl" means an aliphatic hydrocarbon group containing a carbon—carbon triple bond and which may be straight or branched having about 2 to about 15 carbon atoms in the chain. Preferred alkynyl groups have 2 to about 12 carbon atoms in the chain; and more preferably 2 to about 6 carbon atoms (e.g. 2 to 4 carbon atoms) in the chain. Exemplary alkynyl groups include ethynyl, propynyl, n-butynyl, i-butynyl, 3-methylbut-2-ynyl, and n-pentynyl.

"Alkynylene" means an aliphatic bivalent radical derived from a straight or branched alkynyl group, in which the alkynyl group is as described herein. Exemplary alkynylene radicals include ethynylene and propynylene.

"Amino acid side chains" means the substituent found on the carbon between the amino and carboxy groups in α-amino acids. For examples of "corresponding protected derivatives" of amino acid side chains, see T. W. Greene and P. G. M. Wuts in "Protective Groups in Organic Chemistry" John Wiley and Sons, 1991.

"Aroyl" means an aryl-CO— group in which the aryl group is as described herein. Exemplary aroyl groups include benzoyl and 1- and 2-naphthoyl.

"Aroylamino" is an aroyl-NH— group wherein aroyl is as previously defined.

"Aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl or cycloalkenyl group are fused together to form a cyclic structure, such as a tetrahydronaphthyl, indenyl or indanyl ring. Aryl groups may be substituted with one or more aryl group substituents which may be the same or different, where "aryl group substituent" includes, for example, acyl, acylamino, alkoxy, alkoxycarbonyl, alkylenedioxy, alkylsulphinyl, alkylsulphonyl, alkylthio, aroyl, aroylamino, aryl, arylalkyloxy, arylalkyloxycarbonyl, arylalkylthio, aryloxy, aryloxycarbonyl, arylsulphinyl, arylsulphonyl, arylthio, carboxy, cyano, halo, heteroaroyl, heteroaryl, heteroarylalkyloxy, heteroaroylamino, heteroaryloxy, hydroxy, nitro, trifluoromethyl, $Y^3Y^4N$—, $Y^3Y^4NCO$—, $Y^3Y^4NSO_2$—, $Y^3Y^4N$—$C_{2-6}$alkylene-Z— [where Z is O, $NR^4$ or $S(O)_n$], alkylC(=O)—$Y^3N$—, alkyl$SO_2$—$Y^3N$— or alkyl optionally substituted with aryl, heteroaryl, hydroxy, or $Y^3Y^4N$—.

"Arylalkenyl" means an aryl-alkenyl-group in which the aryl and alkenyl are as previously described. Preferred arylalkenyls contain a lower alkenyl moiety. Exemplary arylalkenyl groups include styryl and phenylallyl.

"Arylalkyl" means an aryl-alkyl-group in which the aryl and alkyl moieties are as previously described. Preferred arylalkyl groups contain a $C_{1-4}$alkyl moiety. Exemplary arylalkyl groups include benzyl, 2-phenethyl and naphthlenemethyl.

"Arylalkyloxy" means an arylalkyl-O— group in which the arylalkyl groups is as previously described. Exemplary arylalkyloxy groups include benzyloxy and 1- or 2-naphthalenemethoxy.

"Arylalkyloxycarbonyl" means an arylalkyl-O—CO— group in which the arylalkyl groups is as previously described. An exemplary arylalkyloxycarbonyl group is benzyloxycarbonyl.

"Arylalkylthio" means an arylalkyl-S— group in which the arylalkyl group is as previously described. An exemplary arylalkylthio group is benzylthio.

"Arylalkynyl" means an aryl-alkynyl-group in which the aryl and alkynyl are as previously described. Exemplary arylalkynyl groups include phenylethynyl and 3-phenylbut-2-ynyl.

"Aryldiyl" means an optionally substituted bivalent radical derived from an aryl group. Exemplary aryldiyl groups include optionally substituted phenylene, naphthylene and indanylene. Suitable substituents include one or more "aryl group substituents" as defined above, particularly halogen, methyl or methoxy.

"Aryloxy" means an aryl-O— group in which the aryl group is as previously described. Exemplary aryloxy groups include optionally substituted phenoxy and naphthoxy.

"Aryloxycarbonyl" means an aryl-O—C(=O)— group in which the aryl group is as previously described. Exemplary aryloxycarbonyl groups include phenoxycarbonyl and naphthoxycarbonyl.

"Arylsulphinyl" means an aryl-SO— group in which the aryl group is as previously described.

"Arylsulphonyl" means an aryl-SO$_2$— group in which the aryl group is as previously described.

"Arylsulphonylcarbamoyl" means an aryl-SO$_2$—NH—C(=O)— group in which the aryl group is as previously described.

"Arylthio" means an aryl-S— group in which the aryl group is as previously described. Exemplary arylthio groups include phenylthio and naphthylthio.

"Azaheteroaryldiyl" means a bivalent radical derived from an azaheteroaryl group.

"Azaheteroaryl" means an aromatic carbocyclic moiety of about 5 to about 10 ring members in which one of the ring members is nitrogen and the other ring members are chosen from carbon, oxygen, sulphur, or nitrogen. Examples of azaheteroaryl groups include pyridyl, pyrimidinyl, quinolinyl, isoquinolinyl, quinazolinyl, imidazolyl, and benzimidazolyl.

"Cyclic amine" means a 3 to 8 membered monocyclic cycloalkyl ring system where one of the ring carbon atoms is replaced by nitrogen and which (i) may be optionally substituted with one or more substituents selected from alkoxy, carboxamido, carboxy, hydroxy, oxo (or a 5, 6 or 7 membered cyclic acetal derivative thereof) or R$^8$; (ii) may also contain a further heteroatom selected from O, S, SO$_2$, or NY$^5$ (where Y$^5$ is hydrogen, alkyl, aryl, arylalkyl, —C(=O)—R—, —C(=O)—OR$^{13}$ or —S$_2$R$^{13}$); and (iii) may be fused to additional aryl (e.g. optionally substituted phenyl), heteroaryl (e.g. optionally substituted pyridyl), heterocycloalkyl or cycloalkyl rings to form a bicyclic or tricyclic ring system. Exemplary cyclic amines include pyrrolidinyl, piperidinyl, morpholinyl, piperazinyl, indolinyl, pyrindolinyl, tetrahydroquinolinyl and the like groups. When the group

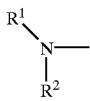

a cyclic amine this may particularly represent a bicyclic ring system consisting of a cyclic amine containing a 5–7 membered monocyclic cycloalkyl group wherein one of the ring carbon atoms is replaced by a nitrogen atom which is fused via ring carbon atoms to an aryl (e.g. optionally substituted phenyl) ring.

"Cycloalkenyl" means a non-aromatic monocyclic or multicyclic ring system containing at least one carbon—carbon double bond and having about 3 to about 10 carbon atoms. Exemplary monocyclic cycloalkenyl rings include cyclopentenyl, cyclohexenyl or cycloheptenyl.

"Cycloalkenylalkyl" means a cycloalkenyl-alkyl-group in which the cycloalkenyl and alkyl moieties are as previously described. Exemplary cycloalkenylalkyl groups include cyclopentenylmethyl, cyclohexenylmethyl or cycloheptenylmethyl.

"Cycloalkenylene" means a bivalent radical derived from a cycloalkenyl group. Exemplary cycloalkenylene radicals include cyclopentenylene and cyclohexenylene.

"Cycloalkyl" means a saturated monocyclic or bicyclic ring system of about 3 to about 10 carbon atoms optionally substituted by oxo. Exemplary monocyclic cycloalkyl rings include C$_{3-8}$cycloalkyl rings such as cyclopropyl, cyclopentyl, cyclohexyl and cycloheptyl.

"Cycloalkylalkyl" means a cycloalkyl-alkyl-group in which the cycloalkyl and alkyl moieties are as previously described. Exemplary monocyclic cycloalkylalkyl groups include cyclopropylmethyl, cyclopentylmethyl, cyclohexylmethyl and cycloheptylmethyl.

"Cycloalkylene" means a bivalent radical derived from a cycloalkyl group. Exemplary cycloalkenylene radicals include cyclopentylene and cyclohexylene.

"Halo" or "halogen" means fluoro, chloro, bromo, or iodo. Preferred are fluoro or chloro.

"Heteroaroyl" means a heteroaryl-C(=O)— group in which the heteroaryl group is as described herein. Exemplary groups include pyridylcarbonyl.

"Heteroaroylamino" means a heteroaroyl-NH— group in which the heteroaryl moiety are as previously described.

"Heteroaryl" as a group or part of a group denotes: (i) an optionally substituted aromatic monocyclic or multicyclic organic moiety of about 5 to about 10 ring members in which one or more of the ring members is/are element(s) other than carbon, for example nitrogen, oxygen or sulphur (examples of such groups include benzimidazolyl, benzthiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl groups, optionally substituted by one or more aryl group substituents as defined above); (ii) an optionally substituted partially saturated multicyclic heterocarbocyclic moiety in which a heteroaryl and a cycloalkyl or cycloalkenyl group are fused together to form a cyclic structure (examples of such groups include pyrindanyl groups). Optional substituents include one or more "aryl group substituents" as defined above.

"Heteroarylalkenyl" means a heteroaryl-alkenyl-group in which the heteroaryl and alkenyl moieties are as previously described. Preferred heteroarylalkenyl groups contain a lower alkenyl moiety. Exemplary heteroarylalkenyl groups include pyridylethenyl and pyridylallyl.

"Heteroarylalkyl" means a heteroaryl-alkyl-group in which the heteroaryl and alkyl moieties are as previously described. Preferred heteroarylalkyl groups contain a C$_{1-4}$alkyl moiety. Exemplary heteroarylalkyl groups include pyridylmethyl.

"Heteroarylalkyloxy" means an heteroarylalkyl-O— group in which the heteroarylalkyl group is as previously described. Exemplary heteroaryloxy groups include optionally substituted pyridylmethoxy.

"Heteroarylalkynyl" means a heteroaryl-alkynyl-group in which the heteroaryl and alkynyl moieties are as previously described. Exemplary heteroarylalkenyl groups include pyridylethynyl and 3-pyridylbut-2-ynyl.

"Heteroaryldiyl" means a bivalent radical derived from a heteroaryl group.

"Heteroaryloxy" means an heteroaryl-O— group in which the heteroaryl group is as previously described. Exemplary heteroaryloxy groups include optionally substituted pyridyloxy.

"Heteroarylsulphonylcarbamoyl" means a heteroaryl-SO$_2$—NH—C(=O)— group in which the heteroaryl group is as previously described.

"Heterocycle" denotes an optionally substituted saturated, partially saturated or fully unsaturated monocyclic organic moiety of 5 or 6 ring members in which one or more of the ring members is/are element(s) other than carbon, for example nitrogen, oxygen or sulphur. Exemplary 5 or 6 membered heterocycles include furyl, imidazolyl, isoxazolyl, isothiazolyl, oxadiazolyl, oxazolyl, oxazinyl, piperidinyl, pyrazinyl, pyridazinyl, pyrazolyl, pyridyl, pyrimidinyl, pyrrolyl, pyrrolidinyl, pyrrolinyl, 1,3,4-thiadiazolyl, thiazolyl, thienyl and triazolyl groups. Optional substituents include one or more "aryl group substituents" as defined above.

"Heterocycloalkyl" means: (i) a cycloalkyl group of about 3 to 7 ring members which contains one or more heteroatoms selected from O, S or $NY^5$ and optionally substituted by oxo; (ii) an partially saturated multicyclic heterocarbocyclic moiety in which an aryl (or heteroaryl ring), each optionally substituted by one or more "aryl group substituents", and a heterocycloalkyl group are fused together to form a cyclic structure (examples of such groups include chromanyl, dihydrobenzofuranyl, indolinyl and pyrindolinyl groups).

"Heterocycloalkylalkyl" means a heterocycloalkyl-alkyl-group in which the heterocycloalkyl and alkyl moieties are as previously described.

"Heterocycloalkylene" means a bivalent radical derived from a heterocycloalkyl group.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively an ester of a compound of formula (I) containing a carboxy group may be convertible by hydrolysis in vivo to the parent molecule.

Suitable esters of compounds of formula (I) containing a hydroxy group, are for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulphonates, ethanesulphonates, benzenesulphonates, p-toluenesulphonates, cyclohexylsulphamates and quinates.

Suitable esters of compounds of formula (I) containing a carboxy group, are for example those described by F. J. Leinweber, Drug Metab. Res., 1987, 18, page 379.

Suitable esters of compounds of formula (I) containing both a carboxy group and a hydroxy group within the moiety —$L^2$—Y, include lactones, formed by loss of water between said carboxy and hydroxy groups. Examples of lactones include caprolactones and butyrolactones.

An especially useful class of esters of compounds of formula (I) containing a hydroxy group, may be formed from acid moieties selected from those described by Bundgaard et. al., J. Med. Chem., 1989, 32, page 2503–2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Where the compound of the invention contains a carboxy group, or a sufficiently acidic bioisostere, base addition salts may be formed and are simply a more convenient form for use; and in practice, use of the salt form inherently amounts to use of the free acid form. The bases which can be used to prepare the base addition salts include preferably those which produce, when combined with the free acid, pharmaceutically acceptable salts, that is, salts whose cations are non-toxic to the patient in pharmaceutical doses of the salts, so that the beneficial inhibitory effects inherent in the free base are not vitiated by side effects ascribable to the cations. Pharmaceutically acceptable salts, including those derived from alkali and alkaline earth metal salts, within the scope of the invention include those derived from the following bases: sodium hydride, sodium hydroxide, potassium hydroxide, calcium hydroxide, aluminium hydroxide, lithium hydroxide, magnesium hydroxide, zinc hydroxide, anmmonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris (hydroxymethyl)aminomethane, tetramethylammonium hydroxide, and the like.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

With reference to formula (I) above, the following are particular and preferred groupings:

$R^1$ may particularly represent $C_{1-4}$alkyl such as methyl or ethyl, especially methyl.

$R^2$ may particularly represent aryl, especially an optionally substituted phenyl, where the optional substituent is an "aryl group substituent" as defined above.

$R^2$ may also particularly represent aryl$C_{1-4}$alkyl such as optionally substituted phenyl$C_{1-4}$alkyl, especially optionally substituted benzyl or optionally substituted 1-phenylethyl, where the optional substituent is an "aryl group substituent" as defined above.

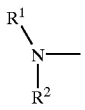

may also particularly represent a cyclic amine containing 5–6 atoms fused to an optionally substituted phenyl ring (where the optional substituent is an "aryl group substituent" as defined above).

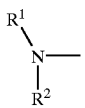

is preferably indolinyl.

Ar$^1$ may particularly represent aryldiyl, and is preferably optionally substituted phenylene, such as optionally substituted m- or p-phenylene, or more preferably optionally substituted p-phenylene (where the optional substituent is an "aryl group substituent" as defined above). Ar$^1$ may especially represent a 3-substituted p-phenylene. Preferred substituents include $C_{1-4}$alkyl, $C_{1-4}$alkoxy, $C_{1-4}$alkylthio, $C_{1-4}$alkysulphinyl and $C_{1-4}$alkylsulphonyl, especially $C_{1-4}$alkoxy (e.g. methoxy).

Ar$^1$ may also particularly represent optionally substituted heteroaryldiyl, such as optionally substituted azaheteroaryldiyl (e.g. optionally substituted pyridinediyl, preferably a p-pyridinediyl), where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group.

L$^1$ may particularly represent a —R$^5$—R$^6$— linkage where R$^5$ represents a straight or branched $C_{1-6}$alkylene chain, especially a straight or branched $C_{1-4}$alkylene chain, and R$^6$ represents —C(=Z$^1$)—NR$^4$—, preferably —C(=O)—NR$^4$—, especially where R$^4$ is hydrogen.

L$^1$ preferably represents —CH$_2$—C(=O)—NH—.

Ar$^2$ may particularly represent azaheteroaryldiyl, especially optionally substituted pyridindiyl, such as p-pyridindiyl (e.g. pyridin-2,5-diyl). Particular optional substituents include $C_{1-4}$alkyl, such as methyl, and $C_{1-4}$alkoxy, such as methoxy.

Ar$^2$ preferably represent optionally substituted phenylene, such as optionally substituted p-phenylene, and is more preferably p-phenylene substituted by lower alkyl (e.g. methyl) or lower alkoxy (e.g. methoxy), or especially unsubstituted p-phenylene.

L$^2$ may particularly represent (a) an optionally substituted alkylene linkage, especially optionally substituted ethylene (b) an unsubstituted alkenylene linkage, especially vinylene or (c) a —Z$^3$—R$^{11}$— linkage, such as —O—CH$_2$—, —S(O)$_n$—CH$_2$—, —S(O)$_n$—CH$_2$—CH$_2$—, —NH—CH$_2$—. Preferred optional substituents within (a) include lower alkyl (e.g. methyl), aryl, heteroaryl, —Z$^2$R$^8$, —N(R$^7$)—C(=O)—R$^8$, —N(R$^7$)—C(=O)—OR$^8$, —N(R$^7$)—SO$_2$—R$^8$, —NY$^1$Y$^2$, —[C(=O)—N(R$^9$)—C(R$^4$)(R$^{10}$)]$_p$—C(=O)—NY$^1$Y$^2$ and alkyl substituted by hydroxy, —OR$^3$, —C(=O)—OR$^7$ or —NY$^1$Y$^2$. L$^2$ is more particularly a $C_{1-4}$alkylene linkage (e.g. ethylene) optionally substituted by lower alkyl (e.g. methyl), aryl, heteroaryl, —Z$^2$R$^8$, —N(R$^7$)—C(=O)—R$^8$, —N(R$^7$)—C(=O)—OR$^8$, —N(R$^7$)—SO$_2$—R$^8$, —NY$^1$Y$^2$, —[C(=O)—N(R$^9$)—C(R$^4$)(R$^{10}$)]$_p$—C(=O)—NY$^1$Y$^2$ or alkyl substituted by hydroxy, —OR$^3$, —C(=O)—OR$^7$ or —NY$^1$Y$^2$. L$^2$ is preferably a group

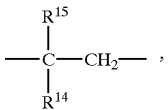

where R$^{15}$ is hydrogen or lower alkyl (e.g. methyl) and R$^{14}$ represents lower alkyl (e.g. methyl), or where R$^{15}$ is hydrogen and R$^{14}$ represents aryl, heteroaryl, —Z$^2$R$^8$, —N(R$^7$)—C(=O)—R$^8$, —N(R$^7$)—C(=O)—OR$^8$, —N(R$^7$)—SO$_2$—R$^8$, —NY$^1$Y$^2$, —[C(=O)—N(R$^9$)—C(R$^4$)(R$^{10}$)]$_p$—C(=O)—NY$^1$Y$^2$ or alkyl substituted by hydroxy, —OR$^3$, —C(=O)—OR$^7$ or —NY$^1$Y$^2$. L$^2$ is more preferably a group

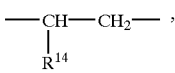

particularly

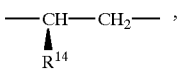

where R$^{14}$ represents lower alkyl (e.g. methyl), aryl, heteroaryl, —Z$^2$R$^8$, —N(R$^7$)—C(=O)—R$^8$, —N(R$^7$)—C(=O)—OR$^8$, —N(R$^7$)—SO$_2$—R$^8$, —NY$^1$Y$^2$, or alkyl substituted by hydroxy, —OR$^3$, —C(=O)—OR$^7$ or —NY$^1$Y$^2$.

Y may particularly represent carboxy.

It is to be understood that this invention covers all appropriate combinations of the particular and preferred groupings referred to herein.

A particular group of compounds of the invention are compounds of formula (Ia):

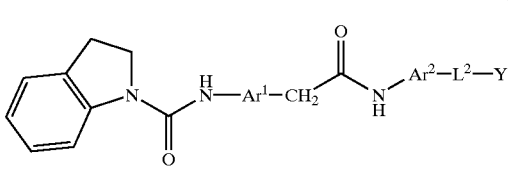

(Ia)

in which Ar$^1$, Ar$^2$, L$^2$ and Y are as hereinbefore defined, and their prodrugs, and pharmaceutically acceptable salts and solvates (e.g. hydrates) of compounds of formula (Ia) and their prodrugs.

Preferred are compounds of formula (Ia) in which Ar$^1$ represents optionally substituted phenylene, such as optionally substituted m- or p-phenylene, preferably optionally substituted p-phenylene (where the optional substituent is an "aryl group substituent" as defined above). Ar$^1$ may especially represent p-phenylene or a 3-substituted p-phenylene. Preferred substituents include $C_{1-4}$alkyl, $C_{1-4}$alkoxy, $C_{1-4}$alkylthio, $C_{1-4}$alkylsulphinyl and $C_{1-4}$alkylsulphonyl, especially $C_{1-4}$alkoxy (e.g. methoxy).

Compounds of formula (Ia) in which Ar$^1$ represents optionally substituted heteroaryldiyl, such as optionally substituted azaheteroaryldiyl (e.g. optionally substituted pyridinediyl, preferably a p-pyridinediyl) where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group are also preferred.

Compounds of formula (Ia) in which Ar² represents azaheteroaryldiyl, especially optionally substituted pyridindiyl, preferably p-pyridindiyl, more preferably pyridin-2,5-diyl are preferred. Preferred optional substituents include $C_{1-4}$alkyl, especially methyl, and $C_{1-4}$alkoxy, especially methoxy.

Compounds of formula (Ia) in which Ar² represents optionally substituted phenylene, such as optionally substituted p-phenylene are also preferred. Preferred optional substituents include lower alkyl (e.g. methyl) or lower alkoxy (e.g. methoxy). Ar² is preferably unsubstituted p-phenylene.

Compounds of formula (Ia) in which L² represents an optionally substituted alkylene chain, especially ethylene or optionally substituted ethylene, are preferred. Preferred optional substituents include lower alkyl (e.g. methyl), aryl, heteroaryl, —Z²R⁸, —N(R⁷)—C(=O)—R⁸, —N(R⁷)—C(=O)—OR⁸, —N(R⁷)—SO—R⁸, —NY¹Y², —[C(=O)—N(R9)—C(R4)(R¹⁰)]_p—C(=O)—NY¹Y² and alkyl substituted by hydroxy, —OR³, —C(=O)—OR⁷ or NY¹Y².

Compounds of formula (Ia) in which L² is a

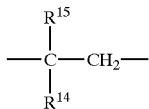

group where R¹⁵ is hydrogen or lower alkyl (e.g. methyl) and R¹⁴ represents lower alkyl (e.g. methyl), or where R¹⁵ is hydrogen and R¹⁴ represents aryl, heteroaryl, —Z²R⁸, —N(R⁷)—C(=O)—R⁸, —N(R⁷)—C(=O)—OR⁸, —N(R⁷)—SO₂—R⁸, NY¹Y², —[C(=O)—N(R⁶)—C(R⁴)(R⁷)]_p—C(=O)-NY¹Y² or alkyl substituted by hydroxy, —OR³, —C(=O)—OR⁷ or NY¹Y² are particularly preferred.

Compounds of formula (Ia) in which L² is a

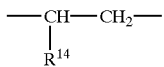

group, particularly

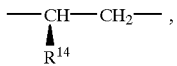

where R¹⁴ represents lower alkyl (e.g. methyl), aryl, heteroaryl, —Z²R⁸, —N(R⁷)—C(=O)—R⁸, —N(R⁷)—C(=O)—OR⁸, —N(R⁷)—SO₂—R⁸, —NY¹Y²,or alkyl substituted by hydroxy, —OR³, —C(=O)—OR⁷ or —NY¹Y² are especially preferred.

Compounds of formula (Ia) in which Y represents carboxy are preferred.

A preferred group of compounds of the invention are compounds of formula (Ia) in which: Ar¹ is p-phenylene or 3-substituted p-phenylene [especially 3-($C_{1-4}$alkoxy)-substituted-p-phenylene such as 3-methoxy-p-phenylene]; Ar² is p-phenylene; L² is a

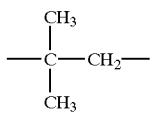

group, or preferably a

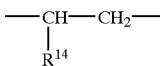

group, particularly

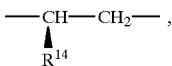

where R¹⁴ is lower alkyl (e.g. methyl), aryl, heteroaryl, —Z²R⁸ (e.g. methoxy), —N(R⁷)—C(=O)—R⁸, —N(R⁷)—C(=O)—OR⁸, —N(R⁷)—SO₂—R⁸, —NY³Y⁴, or alkyl substituted by hydroxy, —OR³, —C(=O)—OR⁷ or —NY¹Y2; Y is carboxy; and the corresponding N-oxides, and their prodrugs; and pharmaceutically acceptable salts and solvates (e.g. hydrates) of such compounds and their N-oxides and prodrugs.

A further particular group of compounds of the invention are compounds of formula (Ib):

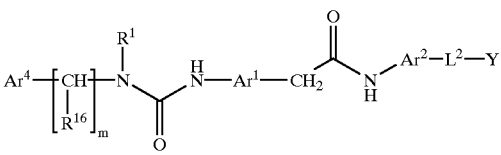

(Ib)

in which Ar¹, Ar², R¹, L² and Y are as hereinbefore defined, R¹⁶ is hydrogen or methyl, Ar⁴ is aryl and in is zero or 1, and their prodrugs, and pharmaceutically acceptable salts and solvates (e.g. hydrates) of compounds of formula (Ib) and their prodrugs.

Compounds of formula (Ib) in which Ar⁴ represents phenyl or phenyl substituted by an "aryl group substituent" as defined above, are preferred, especially unsubstituted phenyl.

Compounds of formula (Ib) in which R¹ represents $C_{1-4}$alkyl, especially methyl or ethyl, are preferred.

Preferred are compounds of formula (Ib) in which Ar¹ represents optionally substituted phenylene, such as optionally substituted m- or p-phenylene, preferably optionally substituted p-phenylene (where the optional substituent is an "aryl group substituent" as defined above). Ar¹ may especially represent p-phenylene or a 3-substituted p-phenylene. Preferred substituents include $C_{1-4}$alkyl, $C_{1-4}$alkoxy, $C_{1-4}$alkylthio, $C_{1-4}$alkylsulphinyl and $C_{1-4}$alkylsulphonyl, especially $C_{1-4}$alkoxy (e.g. methoxy).

Compounds of formula (Ib) in which Ar¹ represents optionally substituted heteroaryldiyl, such as optionally substituted azaheteroaryldiyl (e.g. optionally substituted pyridinediyl, preferably a p-pyridinediyl) where the optional substituents include $C_{1-4}$alkyl and $C_{1-4}$alkoxy, especially methyl and methoxy, more preferably a pyridine-2,5-diyl which is substituted in the 4- or 6-position with a methyl or methoxy group are also preferred.

Compounds of formula (Ib) in which Ar² represents azaheteroaryldiyl, especially optionally substituted pyridindiyl, preferably p-pyridindiyl, more preferably pyridin-2,5-diyl are preferred. Preferred optional substituents include $C_{1-4}$alkyl, especially methyl, and $C_{1-4}$alkoxy, especially methoxy.

Compounds of formula (Ib) in which Ar² represents optionally substituted phenylene, such as optionally substituted p-phenylene are also preferred. Preferred optional substituents include lower alkyl (e.g. methyl) or lower alkoxy (e.g. methoxy). $Ar^2$ is preferably unsubstituted p-phenylene.

Compounds of formula (Ib) in which $L^2$ represents an optionally substituted alkylene chain, especially optionally substituted ethylene, are preferred. Preferred optional substituents include lower alkyl (e.g. methyl), aryl, heteroaryl, $—Z^2R^8$, $—N(R^7)—C(=O)—R^8$, $—N(R^7)—C(=O)—OR^8$, $—N(R^7)—SO_2—R^8$, $—NY^1Y^2$, $—[C(=O)—N(R^9)—C(R^4)(R^{10})]_p—C(=O)-NY^1Y^2$ and alkyl substituted by hydroxy, $—OR^3$, $—C(=O)—OR^7$ or $—NY^1Y^2$.

Compounds of formula (Ib) in which $L^2$ is a

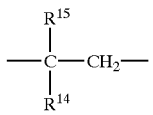

group where $R^{15}$ is hydrogen or lower alkyl (e.g. methyl) and $R^{14}$ represents lower alkyl (e.g. methyl), or where $R^{15}$ is hydrogen and R represents aryl, heteroaryl, $—Z^2R^8$, $—N(R^7)—C(=O)—R^8$, $—N(R^7)—C(=O)—OR^8$, $—N(R^7)—SO_2—R^8$, $—NY^1Y^2$, $—[C(=O)—N(R^6)—C(R^4)(R^7)]_p—C(=O)—NY^1Y^2$ or alkyl substitute by hydroxy, $—OR^3$, $—C(=O)—OR^7$ or $—NY^1Y^2$ are particularly preferred.

Compounds of formula (Ib) in which $L^2$ is a

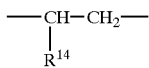

group, particularly

where $R^{14}$ represents lower alkyl (e.g. methyl), aryl, heteroaryl, $—Z^2R^8$, $—N(R^7)—C(=O)—R^8$, $—N(R^7)—C(=O)—OR^8$, $—N(R^7)—SO_2—R^8$, $—NY^1Y^2$, or alkyl substituted by hydroxy, $—OR^3$, $—C(=O)—OR^7$ or $—NY^1Y^2$ are especially preferred.

Compounds of formula (Ib) in which Y represents carboxy are preferred.

A preferred group of compounds of the invention are compounds of formula (Ib) in which: $Ar^4$ is aryl; m is zero or 1; $R^{16}$ is hydrogen or methyl; $R^1$ is $C_{1-4}$alkyl (especially methyl or ethyl); $Ar^1$ is p-phenylene or 3-substituted p-phenylene [especially 3-($C_{1-4}$alkoxy)-substituted-p-phenylene such as 3-methoxy-p-phenylene]; $Ar^2$ is p-phenylene; $L^2$ is a

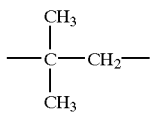

group, or preferably a

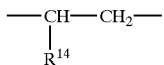

group, particularly

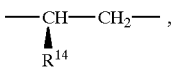

where $R^{14}$ is lower alkyl (e.g. methyl), aryl, heteroaryl, $—Z^2R^8$, $—N(R^7)—C(=O)—R^8$, $—N(R^7)—C(=O)—OR^8$, $—N(R^7)—SO_2—R^8$, $—NY^3Y^4$, or alkyl substituted by hydroxy, $—OR^3$, $—C(=O)—OR^7$ or $—NY^1Y^2$; Y is carboxy; and the corresponding N-oxides, and their prodrugs; and pharmaceutically acceptable salts and solvates (e.g. hydrates) of such compounds and their N-oxides and prodrugs.

Particular compounds of the invention are selected from the following:

3-[4-(2-{4-[(2,3-dihydro-indole-1-carbonyl)-amino]-3-methoxy-phenyl}-acetylamino)-2-pyridyl]-propionic acid;

3-[4-(2-{4-[(2,3-dihydro-indole-1-carbonyl)-amino]-3-methoxy-phenyl}-acetylamino)-phenyl[-butyric acid;

3-[4-({(N-methyl-N-phenyl)amino}carbonyl)-amino)-3-methoxy-phenyl}-acetylamino)-phenyl]-butyric acid;

3-[4-(2-{4-[(2,3-dihydro-indole-1-carbonyl)-amino]-3-methoxy-phenyl}-acetylamino)-phenyl]-3-phenyl-propionic acid;

3-[4-(2-{4-[(2,3-dihydro-indole-1-carbonyl)-amino]-3-methoxy-phenyl}-acetylamino)-phenyl]-3-(4-fluorophenyl)-propionic acid;

3-[4-(2-{4-[(2,3-dihydro-indole-1-carbonyl)-amino]-3-methoxy-phenyl}-acetylamino)-phenyl]-4-methyl-pentanoic acid;

3-[4-(2-{4-[(2,3-dihydro-indole-1-carbonyl)-amino]-3-methoxy-phenyl}-acetylamino)-phenyl]-5-methyl-hexanoic acid;

3-[4-(2-{4-[(2,3-dihydro-indole-1-carbonyl)-amino]-3-methoxy-phenyl}-acetylamino)-phenyl]-4,4-dimethyl-pentanoic acid;

3-(4-{2-[4-(3-methyl-3-o-tolyl-ureido)-phenyl]-acetylamino}-phenyl)-butyric acid;

3-[4-(methyl-{[4-(3-methyl-3-o-tolyl-ureido)-phenyl]-acetyl}-amino)-phenyl]-butyric acid;

3-(4-{2-[3-methoxy-4-(3-methyl-3-o-tolyl-ureido)-phenyl]-acetylamino}-phenyl)-butyric acid;

3-[4-({[3-methoxy-4-(3-methyl-3-o-tolyl-ureido)-phenyl]-acetyl}-methyl-amino)-phenyl]-butyric acid;

3-(4-{2-[3-methyl-4-(3-methyl-3-o-tolyl-ureido)-phenyl]-acetylamino}-phenyl)-butyric acid;

3-[4-(methyl-{[3-methyl-4-(3-methyl-3-o-tolyl-ureido)-pheny]-acetyl-amino)-phenyl]-butyric acid;

3-[4-(2-{4-[(2,3-dihydro-indole-1-carbonyl)-amino)-phenyl}-acetylamino)-phenyl]-butyric acid;

3-{4-[({4-[(2,3-dihydro-indole-1-carbonyl)-amino]-phenyl}-acetyl)-methyl-amino]-phenyl}-butric acid;

3-[4-(2-{4-[(2,3-dihydro-indole-1-carbonyl)-amino]-3-methoxy-phenyl}-acetylamino)-phenyl]-butyric acid;

3-{4-[({4-[(2,3-dihydro-indole-1-carbonyl)-amino]-3-methoxy-phenyl}-acetyl)-methyl-amino]-phenyl}-butyric acid;

3-[4-(2-{4-[(2,3-dihydro-indole-1-carbonyl)-amino]-3-methyl-phenyl}-acetylamino)-phenyl]butyric acid;

3-{4-[({4-[(2,3-dihydro-indole-1-carbonyl)-amino]-3-methyl-phenyl}-acetyl)-methyl-amino]-phenyl}-butyric acid;

3-(3-{2-[4-(3-methyl-3-o-tolyl-ureido)-phenyl]-acetylamino}-phenyl)-butyric acid 3-[3-(methyl-{[4-(3-methyl-3-o-tolyl-ureido)-phenyl]-acetyl}-amino)-phenyl]-butyric acid;

3-(3-{2-[3-methoxy-4-(3-methyl-3-o-tolyl-ureido)-phenyl]-acetylamino}-phenyl)-butyric acid;

3-[3-({[3-methoxy-4-(3-methyl-3-o-tolyl-ureido)-phenyl]-acetyl}-methyl-amino)-phenyl]-butyric acid;

3-(3-{2-[3-methyl-4-(3-methyl-3-o-tolyl-ureido)-phenyl]-acetylamino}-phenyl)-butyric acid;

3-[3-(methyl-{[3-methyl-4-(3-methyl-3-o-tolyl-ureido)-phenyl]-acetyl}-amino)-phenyl]-butyric acid;

3-[3-(2-{4-[(2,3-dihydro-indole-1-carbonyl)-amino]-phenyl}-acetylamino)-phenyl]-butyric acid;

3-{3-[({4-[(2,3-dihydro-indole-1-carbonyl)-amino]-phenyl}-acetyl)-methyl-amino]-phenyl}-butyric acid;

3-[3-(2-{4-[(2,3-dihydro-indole-1-carbonyl)-amino]-3-methoxy-phenyl}-acetylamino)-phenyl]-butyric acid;

3-{3-[({4-[(2,3-dihydro-indole-1-carbonyl)-amino]-3-methoxy-phenyl}-acetyl)-methyl-amino]-phenyl}-butyric acid;

3-[3-(2-{4-[(2,3-dihydro-indole-1-carbonyl)-amino]-3-methyl-phenyl}-acetylamino)-phenyl-butyric acid;

3-{3-[(4-[(2,3-dihydro-indole-1-carbonyl)-amino]-3-methyl-phenyl}-acetyl)-methyl-amino]-phenyl}-butyric acid;

3-benzoylamino-3-[4-(2-{4-[(2,3-dihydro-indole-1-carbonyl)-amino]-phenyl}-acetylamino)-phenyl]-propionic acid;

3-acetylamino-3-[4-(2-{4-[(2,3-dihydro-indole-1-carbonyl)-amino]-phenyl}-acetylamino)-phenyl]-propionic acid;

3-acetylamino-3-[4-(2-{4-[(2,3-dihydro-indole-1-carbonyl)-amino]-3-methoxyphenyl}-acetylamino)-phenyl]-propionic acid;

3-acetylamino-3-[4-({N-methyl-N-(1-phenylethyl)amino}carbonyl)-amino]-3-methoxyphenyl}-acetylamino)-phenyl]-propionic acid;

3-acetylamino-3-[4-({N-benzyl-N-methylamino}carbonyl)-amino]-3-methoxyphenyl}-acetylamino)-phenyl]-propionic acid;

3-acetylamino-3-(4-{2-[4-(3-methyl-3-o-tolyl-ureido)-phenyl]-acetylamino}-phenyl)-propionic acid;

3-benzoylamino-3-(4-{2-[4-(3-methyl-3-o-tolyl-ureido)-phenyl]-acetylamino}-phenyl)-propionic acid;

3-[(5-methyl-isoxazole-3-carbonyl)-amino]-3-(4-{2-[4-(3-methyl-3-o-tolyl-ureido)-phenyl]-acetylamino}-phenyl)-propionic acid;

4-acetylamino-4-(4-{2-[4-(3-methyl-3-o-tolyl-ureido)-phenyl]-acetylamino}-phenyl)-butyric acid;

4-benzoylamino-4-(4-{2-[4-(3-methyl-3-o-tolyl-ureido)-phenyl]-acetylamino}-phenyl)-butyric acid;

4-[(5-methyl-isoxazole-3-carbonyl)-amino]-4-(4-{2-[4-(3-methyl-3-o-tolyl-ureido)-phenyl]-acetylamino}-phenyl)-butyric acid;

4-methoxy-4-(4-{2-[4-(3-methyl-3-o-tolyl-ureido)-phenyl]-acetylamino}-phenyl)-butyric acid;

3-acetylamino-3-[4-(methyl-{[4-(3-methyl-3-o-tolyl-ureido)-phenyl]-acetyl}-amino)-phenyl]-propionic acid;

3-benzoylamino-3-[4-(methyl-{[4-(3-methyl-3-o-tolyl-ureido)-phenyl]-acetyl}-amino)-phenyl]-propionic acid;

3-[(5-methyl-isoxazole-3-carbonyl)-amino]-3-[4-(methyl-{[4-(3-methyl-3-o-tolyl-ureido)-phenyl]-acetyl}-amino)-phenyl]-propionic acid;

4-acetylamino-4-[4-(methyl-{[4-(3-methyl-3-o-tolyl-ureido)-phenyl]-acetyl}-amino)-phenyl]-butyric acid;

4-benzoylamino-4-[4-(methyl-{[4-(3-methyl-3-o-tolyl-ureido)-phenyl]-acetyl}-amino)-phenyl]-butyric acid;

4-[(5-methyl-isoxazole-3-carbonyl)-amino]-4-[4-(methyl-{[4-(3-methyl-3-o-tolyl-ureido)-phenyl-acetyl}-amino)-phenyl]-butyric acid;

4-methoxy-4-[4-(methyl-{[4-(3-methyl-3-o-tolyl-ureido)-phenyl]-acetyl}-amino)-phenyl]-butyric acid;

3-acetylamino-3-(4-{2-[3-methoxy-4-(3-methyl-3-o-tolyl-ureido)-phenyl]-acetylamino}-phenyl)-propionic acid;

3-benzoylamino-3-(4-{2-[3-methoxy-4-(3-methyl-3-o-tolyl-ureido)-phenyl]-acetylamino}-phenyl)-propionic acid;

3-(4-{2-[3-methoxy-4-(3-methyl-3-o-tolyl-ureido)-phenyl]-acetylamino}-phenyl)-3-[(5-methyl-isoxazole-3-carbonyl)-amino]-propionic acid;

4-acetylamino-4-(4-{2-[3-methoxy-4-(3-methyl-3-o-tolyl-ureido)-phenyl]-acetylamino}-phenyl-butyric acid;

4-benzoylamino-4-(4-{2-[3-methoxy4-(3-methyl-3-o-tolyl-ureido)-phenyl]-acetylamino}-phenyl)-butyric acid;

4-(4-{2-[3-methoxy-4-(3-methyl-3-o-tolyl-ureido)-phenyl]-acetylamino}-phenyl)-4-[(5-methyl-isoxazole-3-carbonyl)-amino]-butyric acid;

4-methoxy-4-(4-{2-[3-methoxy-4-(3-methyl-3-o-tolyl-ureido)-phenyl]-acetylamino}-phenyl)-butyric acid;

3-acetylamino-3-[4-({[3-methoxy-4-(3-methyl-3-o-tolyl-ureido)-phenyl]-acetyl}-methyl-amino-phenyl]-propionic acid;

3-benzoylamino-3-[4-({[3-methoxy-4-(3-methyl-3-o-tolyl-ureido)-phenyl]-acetyl}-methyl-amino)-phenyl]-propionic acid;

3-[4-({[3-methoxy-4-(3-methyl-3-o-tolyl-ureido)-phenyl]-acetyl}-methyl-amino)-phenyl]-3-[(5-methyl-isoxazole-3-carbonyl)-amino]-propionic acid;

4-acetylamino-4-[4-({[3-methoxy-4-(3-methyl-3-o-tolyl-ureido)-phenyl]-acetyl}-methyl-amino)-phenyl]-butyric acid;

4-benzoylamino-4-[4-({[3-methoxy-4-(3-methyl-3-o-tolyl-ureido)-phenyl]-acetyl}-methyl-amino)-phenyl]-butyric acid;

4-[4-({[3-methoxy-4-(3-methyl-3-o-tolyl-ureido)-phenyl]-acetyl}-methyl-amino)-phenyl]-4-[(5-methyl-isoxazole-3-carbonyl)-amino]-butyric acid;

4-methoxy-4-[4-({[3-methoxy-4-(3-methyl-3-o-tolyl-ureido)-phenyl]-acetyl}-methyl-amino)-phenyl]-butyric acid;

3-acetylamino-3-[4-(2-{4-[(2,3-dihydro-indole-1-carbonyl)-amino]-phenyl}-acetylamino)-phenyl]-propionic acid;

3-benzoylamino-3-[4-(2-{4-[(2,3-dihydro-indole-1-carbonyl)-amino]-phenyl}-acetylamino)-phenyl]-proplonic acid;

3-[4-(2-{4-[(2,3-dihydro-indole-1-carbonyl)-amino]-phenyl}-acetylamino)-phenyl]-3-[(5-methyl-isoxazole-3-carbonyl)-amino]-propionic acid;

4-acetylamino-4-[4-(2-{4-[(2,3-dihydro-indole-1-carbonyl)-amino]-phenyl}-acetylamino)-phenyl]-butyric acid;

4-benzoylamino-4-[4-(2-{4-[(2,3-dihydro-indole-1-carbonyl)-amino]-phenyl}-acetylamino)-phenyl]-butyric acid;

4-[4-(2-{4-[(2,3-dihydro-indole-1-carbonyl)-amino]-phenyl}-acetylamino)-phenyl]-4-[(5-methyl-isoxazole-3-carbonyl)-amino]-butyric acid;

4-[4-(2-{4-[(2,3-dihydro-indole-1-carbonyl)-amino]-phenyl}-acetylamino)-phenyl]-4-methoxy-butyric acid;

3-acetylamino-3-{4-[({4-[(2,3-dihydro-indole-1-carbonyl)-amino]-phenyl}-acetyl)-methyl-amino]-phenyl}-propionic acid;

3-benzoylamino-3-{4-[({4-[(2,3-dihydro-indole-1-carbonyl)-amino]-phenyl}-acetyl)-methyl-amino]-phenyl}-propionic acid;

3-{4-[({4-[(2,3-dihydro-indole-1-carbonyl)-amino]-phenyl}-acetyl)-methyl-amino]-phenyl}-3-[(5-methyl-isoxazole-3-carbonyl)-amino]-propionic acid;

4-acetylamino-4-{4-[({4-[(2,3-dihydro-indole-1-carbonyl)-amino]-phenyl}-acetyl)-methyl-amino]-phenyl}-butyric acid;
4-benzoylamino-4-{4-[({4-[(2,3-dihydro-indole-1-carbonyl)-amino]-phenyl}-acetyl)-methyl-amino]-phenyl}-butyric acid;
4-{4-[({4-[(2,3-dihydro-indole-1-carbonyl)-amino]-phenyl}-acetyl)-methyl-amino]-phenyl}-4-[(5-methyl-isoxazole-3-carbonyl)-amino]-butyric acid;
4-{4-[({4-[(2,3-dihydro-indole-1-carbonyl)-amino]-phenyl}-acetyl)-methyl-amino]-phenyl}-4-methoxy-butyric acid;
3-acetylamino-3-[4-(2-{4-[(2,3-dihydro-indole-1-carbonyl)-amino]-3-methoxy-phenyl}-acetylamino)-phenyl]-propionic acid;
3-benzoylamino-3-[4-(2-{4-[(2,3-dihydro-indole-1-carbonyl)-amino]-3-methoxy-phenyl}-acetylamino)-phenyl]-propionic acid;
3-[4-(2-{4-[(2,3-dihydro-indole-1-carbonyl)-amino]-3-methoxy-phenyl}-acetylamino)-phenyl]-3-[(5-methyl-isoxazole-3-carbonyl)-amino]-propionic acid;
4-acetylamino-4-[4-(2-{4-[(2,3-dihydro-indole-1-carbonyl)-amino]-3-methoxy-phenyl}-acetylamino)-phenyl]-butyric acid;
4-benzoylamino-4-[4-(2-{4-[(2,3-dihydro-indole-1-carbonyl)-amino]-3-methoxy-phenyl}-acetylamino)-phenyl]-butyric acid;
4-[4-(2-{4-[(2,3-dihydro-indole-1-carbonyl)-amino]-3-methoxy-phenyl}-acetylamino)-phenyl]-4-[(5-methyl-isoxazole-3-carbonyl)-amino]-butyric acid;
4-[4-(2-{4-[(2,3-dihydro-indole-1-carbonyl)-amino]-3-methoxy-phenyl}-acetylamino)-phenyl]-4-methoxy-butyric acid;
3-acetylamino-3-{4-[({4-[(2,3-dihydro-indole-1-carbonyl)-amino]-3-methoxy-phenyl}-acetyl)-methyl-amino]-phenyl}-propionic acid;
3-benzoylamino-3-{4-[({4-[(2,3-dihydro-indole-1-carbonyl)-amino]-3-methoxy-phenyl}-acetyl)-methyl-amino]-phenyl}-propionic acid;
3-{4-[({4-[(2,3-dihydro-indole-1-carbonyl)-amino]-3-methoxy-phenyl}-acetyl)-methyl-amino]-phenyl}-3-[(5-methyl-isoxazole-3-carbonyl)-amino]-propionic acid;
4-acetylamino-4-{4-[({4-[(2,3-dihydro-indole-1-carbonyl)-amino]-3-methoxy-phenyl}-acetyl)-methyl-amino]-phenyl}-butyric acid;
4-benzoylamino-4-{4-[({4-[(2,3-dihydro-indole-1-carbonyl)-amino]-3-methoxy-phenyl}-acetyl)-methyl-amino]-phenyl}-butyric acid;
4-{4-[({4-[(2,3-dihydro-indole-1-carbonyl)-amino]-3-methoxy-phenyl}-acetyl)-methyl-amino]-phenyl}-4-[(5-methyl-isoxazole-3-carbonyl)-amino]-butyric acid;
4-{4-[({4-[(2,3-dihydro-indole-1-carbonyl)-amino]-3-methoxy-phenyl}-acetyl)-methyl-amino]-phenyl}-4-methoxy-butyric acid;
3-acetylamino-3-(3-{2-[4-(3-methyl-3-o-tolyl-ureido)-phenyl]-acetylamino}-phenyl)-propionic acid;
3-benzoylamino-3-(3-{2-[4-(3-methyl-3-o-tolyl-ureido)-phenyl]-acetylamino}-phenyl)-propionic acid;
3-[(5-methyl-isoxazole-3-carbonyl)-amino]-3-(3-{2-[4-(3-methyl-3-o-tolyl-ureido)-phenyl]-acetylamino}-phenyl)-propionic acid;
4-acetylamino-4-(3-{2-[4-(3-methyl-3-o-tolyl-ureido)-phenyl]-acetylamino}-phenyl)-butyric acid;
4-benzoylamino-4-(3-{2-[4-(3-methyl-3-o-tolyl-ureido)-phenyl]-acetylamino}-phenyl)-butyric acid;
4-[(5-methyl-isoxazole-3-carbonyl)-amino]-4-(3-{2-[4-(3-methyl-3-o-tolyl-ureido)-phenyl]-acetylamino}-phenyl)-butyric acid;
4-methoxy-4-(3-{2-[4-(3-methyl-3-o-tolyl-ureido)-phenyl]-acetylamino}-phenyl)-butyric acid;
3-acetylamino-3-[3-(methyl-{[4-(3-methyl-3-o-tolyl-ureido)-phenyl]-acetyl}-amino)-phenyl]-propionic acid;
3-benzoylamino-3-[3-(methyl-{[4-(3-methyl-3-o-tolyl-ureido)-phenyl]-acetyl}-amino)-phenyl]-propionic acid;
3-[(5-methyl-isoxazole-3-carbonyl)-amino]-3-[3-(methyl-{[4-(3-methyl-3-o-tolyl-ureido)-phenyl]-acetyl}-amino)-phenyl]-propionic acid;
4-acetylamino-4-[3-(methyl-{[4-(3-methyl-3-o-tolyl-ureido)-phenyl]-acetyl}-amino)-phenyl]-butyric acid;
4-benzoylamino-4-[3-(methyl-{[4-(3-methyl-3-o-tolyl-ureido)-phenyl]-acetyl}-amino)-phenyl]-butyric acid;
4-[(5-methyl-isoxazole-3-carbonyl)-amino]-4-[3-(methyl-{[4-(3-methyl-3-o-tolyl-ureido)phenyl]-acetyl}-amino)-phenyl]-butyric acid;
4-methoxy-4-[3-(methyl-{[4-(3-methyl-3-o-tolyl-ureido)-phenyl]-acetyl}-amino)-phenyl]-butyric acid;
3-acetylamino-3-(3-{2-[3-methoxy-4-(3-methyl-3-o-tolyl-ureido)-phenyl]-acetylamino}-phenyl)-propionic acid;
3-benzoylamino-3-(3-{2-[3-methoxy-4-(3-methyl-3-o-tolyl-ureido)-phenyl]-acetylamino}-phenyl)-propionic acid;
3-(3-{2-[3-methoxy-4-(3-methyl-3-o-tolyl-ureido)-phenyl]-acetylamino}-phenyl)-3-[(5-methyl-isoxazole-3-carbonyl)-amino]-propionic acid;
4-acetylamino-4-(3-{2-[3-methoxy-4-(3-methyl-3-o-tolyl-ureido)-phenyl]-acetylamino}-phenyl)-butyric acid;
4-benzoylamino-4-(3-{2-[3-methoxy-4-(3-methyl-3-o-tolyl-ureido)-phenyl]-acetylamino}-phenyl)-butyric acid;
4-(3-{2-[3-methoxy-4-(3-methyl-3-o-tolyl-ureido)-phenyl]-acetylamino}-phenyl)-4-[(5-methyl-isoxazole-3-carbonyl)-amino]-butyric acid;
4-methoxy-4-(3-{2-[3-methoxy-4-(3-methyl-3-o-tolyl-ureido)-phenyl]-acetylamino}-phenyl)-butyric acid;
3-acetylamino-3-[3-({[3-methoxy-4-(3-methyl-3-o-tolyl-ureido)-phenyl]-acetyl}-methyl-amino)-phenyl]-propionic acid;
3-benzoylamino-3-[3-({[3-methoxy-4-(3-methyl-3-o-tolyl-ureido)-phenyl]-acetyl}-methyl-amino)-phenyl]-propionic acid;
3-[3-({[3-methoxy-4-(3-methyl-3-o-tolyl-ureido)-phenyl]-acetyl}-methyl-amino)-phenyl]-3-[(5-methyl-isoxazole-3-carbonyl)-amino]-propionic acid;
4-acetylamino-4-[3-({[3-methoxy-4-(3-methyl-3-o-tolyl-ureido)-phenyl]-acetyl}-methyl-amino)-phenyl]-butyric acid;
4-benzoylamino-4-[3-({[3-methoxy-4-(3-methyl-3-o-tolyl-ureido)-phenyl]-acetyl}-methyl-amino)-phenyl]-butyric acid;
4-[3-({[3-methoxy-4-(3-methyl-3-o-tolyl-ureido)-phenyl]-acetyl}-methyl-amino)-phenyl]-4-[(5-methyl-isoxazole-3-carbonyl)-amino]-butyric acid;
4-methoxy-4-[3-({[3-methoxy-4-(3-methyl-3-o-tolyl-ureido)-phenyl]-acetyl}-methyl-amino)-phenyl]-butyric acid;
3-acetylamino-3-[3-(2-{4-[(2,3-dihydro-indole-1-carbonyl)-amino]-phenyl}-acetylamino)-phenyl]-propionic acid;
3-benzoylamino-3-[3-(2-{4-[(2,3-dihydro-indole-1-carbonyl)-amino]-phenyl}-acetylamino)-phenyl]-propionic acid;
3-[3-(2-{4-[(2,3-dihydro-indole-1-carbonyl)-amino]-phenyl}-acetylamino)-phenyl]-3-[(5-methyl-isoxazole-3-carbonyl)-amino]-propionic acid;
4-acetylamino-4-[3-(2-{4-[(2,3-dihydro-indole-1-carbonyl)-amino]-phenyl}-acetylamino)-phenyl]-butyric acid;

4-benzoylamino-4-[3-(2-{4-[(2,3-dihydro-indole-1-carbonyl)-amino]-phenyl}-acetylamino)-phenyl]-butyric acid;

4-[3-(2-{4-[(2,3-dihydro-indole-1-carbonyl)-amino]-phenyl}-acetylamino)-phenyl]-4-[(5-methyl-isoxazole-3-carbonyl)-amino]-butyric acid;

4-[3-(2-{4-[(2,3-dihydro-indole-1-carbonyl)-amino]-phenyl}-acetylamino)-phenyl]-4-methoxy-butyric acid;

3-acetylamino-3-{3-[({4-[(2,3-dihydro-indole-1-carbonyl)-amino]-phenyl}-acetyl)-ethyl-amino]-phenyl}-propionic acid;

3-benzoylamino-3-{3-[({4-[(2,3-dihydro-indole-1-carbonyl)-amino]-phenyl}-acetyl)-ethyl-amino]-phenyl}-propionic acid;

3-{3-[({4-[(2,3-dihydro-indole-1-carbonyl)-amino]-phenyl}-acetyl)-methyl-amino]-phenyl}-3-[(5-methyl-isoxazole-3-carbonyl)-amino]-propionic acid;

4-acetylamino-4-{3-[({4-[(2,3-dihydro-indole-1-carbonyl)-amino]-phenyl}-acetyl)-methyl-amino]-phenyl}-butyric acid;

4-benzoylamino-4-{3-[({4-[(2,3-dihydro-indole-1-carbonyl)-amino]-phenyl}-acetyl)-methyl-amino]-phenyl}-butyric acid;

4-{3-[({4-[(2,3-dihydro-indole-1-carbonyl)-amino]-phenyl}-acetyl)-methyl-amino]-phenyl}-4-[(5-methyl-isoxazole-3-carbonyl)-amino]-butyric acid;

4-{3-[({4-[(2,3-dihydro-indole-1-carbonyl)-amino]-phenyl}-acetyl)-methyl-amino]-phenyl}-4-methoxy-butyric acid;

3-acetylamino-3-[3-(2-{4-[(2,3-dihydro-indole-1-carbonyl)-amino]-3-methoxy-phenyl}-acetylamino)-phenyl]-propionic acid;

3-benzoylamino-3-[3-(2-{4-[(2,3-dihydro-indole-1-carbonyl)-amino]-3-methoxy-phenyl}-acetylamino)-phenyl]-propionic acid;

3-[3-(2-{4-[(2,3-dihydro-indole-1-carbonyl)-amino]-3-methoxy-phenyl}-acetylamino)-phenyl]-3-[(5-methyl-isoxazole-3-carbonyl)-amino]-propionic acid;

4-acetylamino-4-[3-(2-{4-[(2,3-dihydro-indole-1-carbonyl)-amino]-3-methoxy-phenyl}-acetylamino)-phenyl]-butyric acid;

4-benzoylamino-4-[3-(2-{4-[(2,3-dihydro-indole-1-carbonyl)-amino]-3-methoxy-phenyl}-acetylamino)-phenyl]-butyric acid;

4-[3-(2-{4-[(2,3-dihydro-indole-1-carbonyl)-amino]-3-methoxy-phenyl}-acetylamino)-phenyl]-4-[(5-methyl-isoxazole-3-carbonyl)-amino]-butyric acid;

4-[3-(2-{4-[(2,3-dihydro-indole-1-carbonyl)-amino]-3-methoxy-phenyl}-acetylamino)-phenyl]-4-methoxy-butyric acid;

3-acetylamino-3-{3-[({4-[(2,3-dihydro-indole-1-carbonyl)-amino]-3-methoxy-phenyl}-acetyl)-methyl-amino]-phenyl}-propionic acid;

3-benzoylamino-3-{3-[({4-[(2,3-dihydro-indole-1-carbonyl)-amino]-3-methoxy-phenyl}methyl-amino]-phenyl}-propionic acid;

3-{3-[({4-[(2,3-dihydro-indole-1-carbonyl)-amino]-3-methoxy-phenyl}-acetyl)-methyl-amino]-phenyl}-3-[(5-methyl-isoxazole-3-carbonyl)-amino]-propionic acid;

4-acetylamino-4-{3-[({4-[(2,3-dihydro-indole-1-carbonyl)-amino]-3-methoxy-phenyl}-acetyl)-methyl-amino]-phenyl}-butyric acid;

4-benzoylamino-4-{3-[({4-[(2,3-dihydro-indole-1-carbonyl)-amino]-3-methoxy-phenyl}-acetyl)-methyl-amino]-phenyl}-butyric acid;

4-{3-[({4-[(2,3-dihydro-indole-1-carbonyl)-amino]-3-methoxy-phenyl}-acetyl)-methyl-amino]-phenyl}-4-[(5-methyl-isoxazole-3-carbonyl)-amino]-butyric acid;

4-{3-[({4-[(2,3-dihydro-indole-1-carbonyl)-amino]-3-methoxy-phenyl}-acetyl)-methyl-amino]-phenyl}-4-methoxy-butyric acid;

and the corresponding N-oxides, and their prodrugs; and pharmaceutically acceptable salts and solvates (e.g. hydrates) of such compounds and their N-oxides and prodrugs.

Preferred compounds of the invention are:

3-[4-(2-{4-[(2,3-dihydro-indole-1-carbonyl)-amino]-3-methoxy-phenyl}-acetylamino)-phenyl]-butyric acid;

3-[4-({(N-methyl-N-phenyl)amino}carbonyl)-amino)-3-methoxy-phenyl}-acetylamino)-phenyl]-butyric acid;

3-benzoylamino-3-[4-(2-{4-[(2,3-dihydro-indole-1-carbonyl)-amino]-phenyl}-acetylamino)-phenyl]-propionic acid;

3-acetylamino-3-[4-(2-{4-[(2,3-dihydro-indole-1-carbonyl)-amino]-phenyl}-acetylamino)-phenyl]-propionic acid;

3-acetylamino-3-[4-(2-{4-[(2,3-dihydro-indole-1-carbonyl)-amino]-3-methoxyphenyl}-acetylamino)-phenyl]-propionic acid;

3-acetylamino-3-[4-({N-methyl-N-(1-phenylethyl)amino}carbonyl)-amino]-3-methoxyphenyl}-acetylamino)-phenyl]-propionic acid;

3-acetylamino-3-[4-({N-benzyl-N-methylamino}carbonyl)-amino]-3-methoxyphenyl}-acetylamino)-phenyl]-propionic acid;

3-[4-(2-{4-[(2,3-dihydro-indole-1-carbonyl)-amino]-3-methoxy-phenyl}-acetylamino)-phenyl]-butyric acid;

3-[4-(2-{4-[(2,3-dihydro-indole-1-carbonyl)-amino]-3-methoxy-phenyl}-acetylamino)-phenyl]-butyric acid;

and the corresponding N-oxides, and their prodrugs; and pharmaceutically acceptable salts and solvates (e.g. hydrates) of such compounds and their N-oxides and prodrugs.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention block the interaction of the ligand VCAM-1 to its integrin receptor VLA-4 (α4β1) according to tests described in the literature and described in vitro and in vivo procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of an inhibitor of α4β1 mediated cell adhesion. For example, compounds of the present invention are useful in the treatment of inflammatory diseases, for example joint inflammation, including arthritis, rheumatoid arthritis and other arthritic conditions such as rheumatoid spondylitis, gouty arthritis, traumatic arthritis, rubella arthritis, psoriatic arthritis and osteoarthritis. Additionally, the compounds are useful in the treatment of acute synovitis, autoimmune diabetes, autoimmune encephalomyelitis, collitis, atherosclerosis, peripheral vascular disease, cardiovascular disease, multiple sclerosis, asthma, psoriasis restenosis, myocarditis, inflammatory bowel disease and melanoma cell division in metastasis.

A special embodiment of the therapeutic methods of the present invention is the treating of asthma.

Another special embodiment of the therapeutic methods of the present invention is the treating of joint inflammation.

Another special embodiment of the therapeutic methods of the present invention is the treating of inflammatory bowel disease.

According to a further feature of the invention there is provided a method for the treatment of a human or animal patient suffering from, or subject to, conditions which can be ameliorated by the administration of an inhibitor of the interaction of the ligand VCAM-1 to its integrin receptor VLA-4 ($\alpha 4\beta 1$), for example conditions as hereinbefore described, which comprises the administration to the patient of an effective amount of compound of the invention or a composition containing a compound of the invention. "Effective amount" is meant to describe an amount of compound of the present invention effective in inhibiting the interaction of the ligand VCAM-1 to its integrin receptor VLA-4 ($\alpha 4\beta 1$), and thus producing the desired therapeutic effect.

References herein to treatment should be understood to include prophylactic therapy as well as treatment of established conditions.

The present invention also includes within its scope pharmaceutical compositions comprising at least one of the compounds of the invention in association with a pharmaceutically acceptable carrier or excipient.

Compounds of the invention may be administered by any suitable means. In practice compounds of the present invention may generally be administered parenterally, topically, rectally, orally or by inhalation, especially by the oral route.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

In a process A compounds of formula (I), containing an amide bond may be prepared by coupling of an acid (or an acid halide) with an amine to give an amide bond using standard peptide coupling procedures as described hereinafter.

As an example of process A, compounds of formula (I) wherein $R^1$, $R^2$, $Ar^1$, $Ar^2$ and $L^2$ are as hereinbefore defined, $L^1$ represents —$R^5$—$R^6$— (in which $R^5$ is as hereinbefore defined and $R^6$ is —C(=O)—$NR^4$—) and Y is carboxy may be prepared by:

(i) coupling HMBA-AM resin with an acid of formula (II) wherein $R^4$, $Ar^2$ and $L^2$ are as hereinbefore defined and $R^{17}$ is a suitable amino-protecting group (such as tertiary-butoxycarbonyl) using peptide coupling conditions, for example reaction in the presence of O-(7-azabenzotriazol-1-yl)-1,1,3,3-tetramethyluronium hexafluorophosphate and diisopropylethylamine in dimethylformamide, at room temperature, to give Resin 1 wherein $R^4$, $Ar^2$, $L^2$ and $R^{17}$ are as hereinbefore defined, $L^3$ is

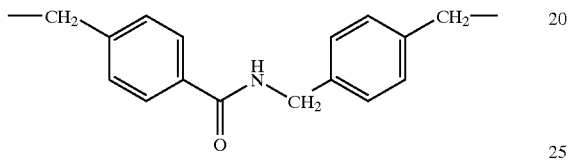

and ⬤P represents the polymeric core (comprising polystyrene crosslinked with 1% to 2% divinylbenzene);

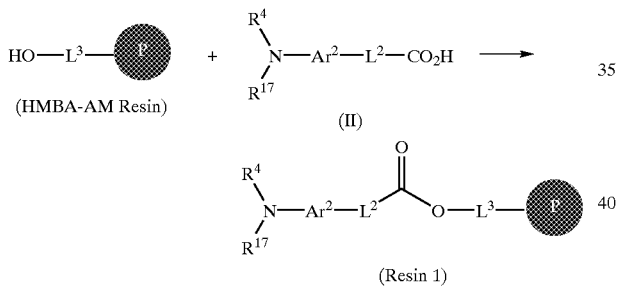

(ii) treatment of Resin 1 with trifluoroacetic acid in an inert solvent such as dichloromethane and at a temperature at about room temperature to give Resin 2 wherein $R^4$, $Ar^2$, $L^2$, $L^3$ and ⬤P are as hereinbefore defined;

(Resin 2)

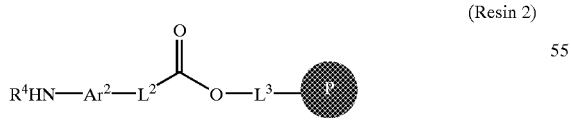

(iii) coupling Resin 2 with an acid of formula (III) wherein $R^6$, $R^{17}$ and $Ar^1$ are as hereinbefore defined, using peptide coupling conditions, for example those described hereinbefore, to give Resin 3 wherein $R^4$, $R^5$, $R^{17}$, $Ar^1$, $Ar^2$, $L^2$, $L^3$ and ⬤P are as hereinbefore defined;

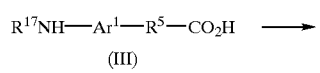

(III)

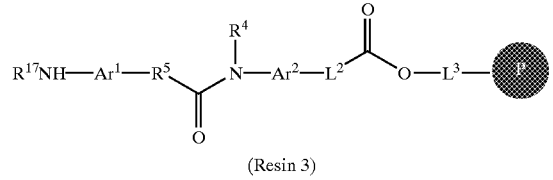

(Resin 3)

(iv) treatment of Resin 3 with trifluoroacetic acid in an inert solvent such as dichloromethane and at a temperature at about room temperature to give Resin 4 wherein $R^4$, $R^5$, $Ar^1$, $Ar^2$, $L^2$, $L^3$ and ⬤P are as hereinbefore defined;

(Resin 4)

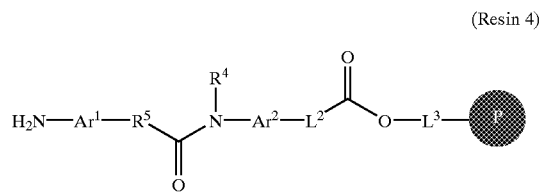

(v) treatment of Resin 4 with an aryl chloroformate, such as 4-nitrophenyl-chloroformate, in the presence of diisopropylethylamine in an inert solvent or preferably a mixture of inert solvents, such as tetrahydrofuran and dichloromethane, at a temperature at about room temperature followed by treatment with amines of formula (IV) wherein $R^1$ and $R^2$ are as hereinbefore defined, in an inert solvent such as dichloromethane and at a temperature at about room temperature to give Resin 5 in which $R^1$, $R^2$, $R^3$, $R^5$, $R^6$, $Ar^1$, $L^2$, $L^3$ and ⬤P are as defined hereinbefore;

(Resin 4)

(i) 4-nitrophenylchloroformate (ii) $R^1$—NH—$R^2$ (IV)

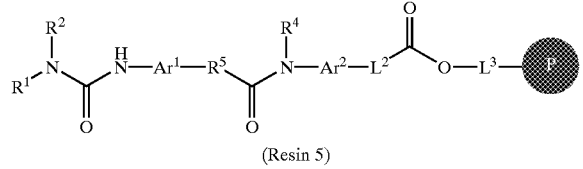

(Resin 5)

[Alternatively Resin 4 may be treated with triphosgene, in the presence of diisopropylethylamine, followed by reaction with amines of formula (IV) to give Resin 5]

(vi) treatment of Resin 5 with aqueous sodium hydroxide in a mixture of inert solvents, such as tetrahydrofuran and methanol, and at a temperature at about room temperature.

As another example of process A, compounds of formula (I) wherein $R^1$, $R^2$, $Ar^1$ and $Ar^2$ are as hereinbefore defined, $L^1$ represents —$R^5$—$R^6$— (in which $R^5$ is as hereinbefore defined and $R^6$ is —C(=O)—NH—), $L^1$ contains a —N($R^7$)—C(=O)—$R^8$ group (in which $R^7$ and $R^8$ are as hereinbefore defined) and Y is carboxy may be prepared by:

(i) treating bromo-Wang resin (4-bromomethyl-phenoxylated styrene/divinylbenzene copolymer) with an acid of formula (V) wherein $Ar^2$ is as hereinbefore defined and $L^2$ contains a —N($R^7$)—$R^{17}$ group in which $R^{17}$ is a suitable imino-protecting group, such as 9H-fluoren-9-ylmethoxylcarbonyl, in the presence of a tertiary amine, such as diisopropylethylamine, and cesium iodide, in an inert solvent, such as dimethylformamide, at a temperature at about room temperature, to give Resin 6 wherein $Ar^2$ is as hereinbefore defined, $L^2$ contains a —N($R^7$)—$R^{17}$ group (in which $R^{17}$ is as just defined) and  represents the polymeric core comprising polystyrene crosslinked with 1% to 2% divinylbenzene;

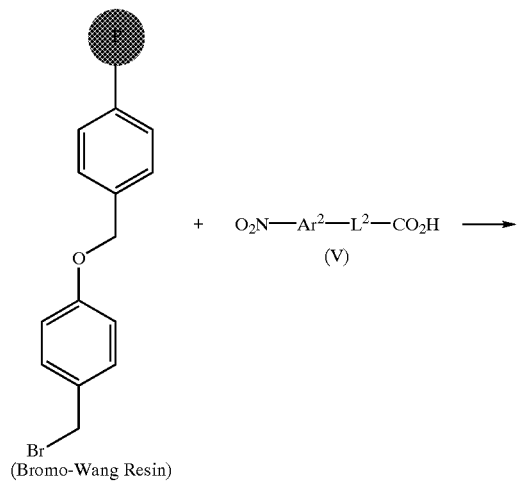

(Bromo-Wang Resin)

(ii) treatment of Resin 6 in which $L^2$ contains a —N($R^7$)—$R^{17}$ group with piperidine in an inert solvent, such as dimethylformamide, and at a temperature at about room temperature to give Resin 6 in which $L^2$ contains a —N($R^7$)H group;

(iii) Reaction of Resin 6 in which $L^2$ contains a —N($R^7$)H group with compounds of formula (VI):

$$R^8-C(=O)-X^1 \qquad (VI)$$

wherein $R^8$ is as hereinbefore defined and $X^1$ is a hydroxy group or a halogen, preferably chlorine, atom to give Resin 6 in which $L^2$ contains a —N($R^7$)—C(=O)—$R^8$ group [When $X^1$ is a hydroxy group the reaction may be carried out using standard peptide coupling procedures for example coupling in the presence of O-(7-azabenzotriazol-1-yl)-1,1,3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature];

(iv) treatment of Resin 6 in which $L^2$ contains a —N($R^7$)—C(=O)—$R^8$ group with a solution of tin (II) chloride in dimethylformamide to give Resin 7 wherein $Ar^2$ and  are as hereinbefore defined and $L^2$ contains a —N($R^7$)—C(=O)—$R^8$ group (in which $R^7$ and $R^8$ are as hereinbefore defined);

(Resin 7)

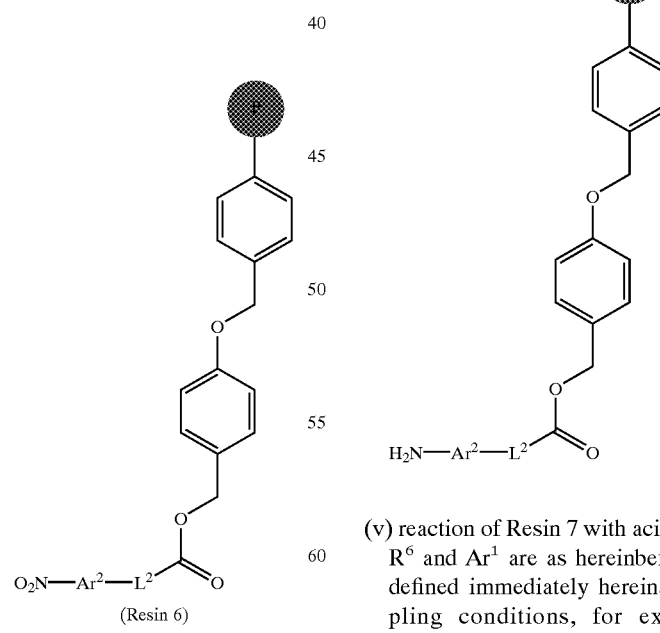

(v) reaction of Resin 7 with acids of formula (III) wherein $R^6$ and $Ar^1$ are as hereinbefore defined and $R^{17}$ is as defined immediately hereinabove, using peptide coupling conditions, for example those described hereinbefore, to give Resin 8 wherein $Ar^1$, $Ar^2$, $L^2$ and  are as hereinbefore defined and $R^{17}$ is as defined immediately hereinabove;

(Resin 8)

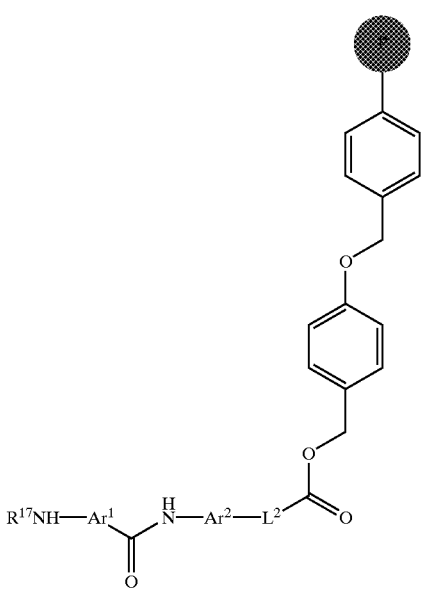

(v) reaction of Resin 7 with diisopropylethylamine followed by triphosgene and subsequent reaction with an amine of formula (IV) wherein $R^1$ and $R^2$ are as hereinbefore defined to give Resin 9 wherein $Ar^1$, $Ar^2$, $L^2$ and P are as hereinbefore defined;

(Resin 9)

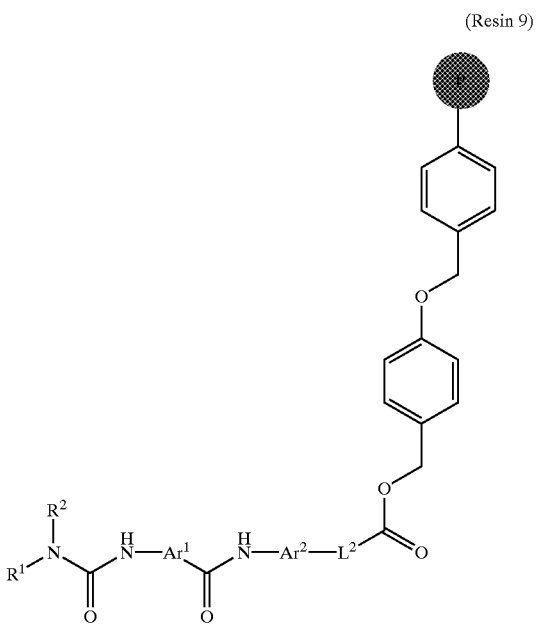

(vi) treatment of Resin 9 with trifluoroacetic acid in an inert solvent, such as dichloromethane, and at a temperature at about room temperature.

Compounds of formula (I) wherein $R^1$, $R^2$, $Ar^1$, $Ar^2$, $L^1$ and $L^2$ are as hereinbefore defined, and Y is carboxy may be prepared by hydrolysis of esters of formula (I) wherein $R^1$, $R^2$, $Ar^1$, $Ar^2$, $L^1$ and $L^2$ are as hereinbefore defined and where the Y is a —$CO_2R^{18}$ group (in which $R^{18}$ is alkyl, alkenyl or arylalkyl). The hydrolysis may conveniently be carried out by alkaline hydrolysis using a base, such as an alkali metal hydroxide, e.g. lithium hydroxide, or an alkali metal carbonate, e.g. potassium carbonate, in the presence of an aqueous/organic solvent mixture, using organic solvents such as dioxan, tetrahydrofuran or methanol, at a temperature from about ambient to about reflux. The hydrolysis of the esters may also be carried out by acid hydrolysis using an inorganic acid, such as hydrochloric acid, in the presence of an aqueous/inert organic solvent mixture, using organic solvents such as dioxan or tetrahydrofuran, at a temperature from about 50° C. to about 80° C.

As another example compounds of formula (I) wherein $R^1$, $R^2$, $Ar^1$, $Ar^2$, $L^1$ and $L^2$ are as hereinbefore defined, and Y is carboxy may be prepared by acid catalysed removal of the tert-butyl group of tert-butyl esters of formula (I) where $R^1$, $R^2$, $Ar^1$, $Ar^2$, $L^1$, $L^2$ are as hereinbefore defined and Y is a —$CO_2R^{18}$ group (in which $R^{18}$ is tert-butyl), using standard reaction conditions, for example reaction with trifluoroacetic acid at a temperature at about room temperature.

As another example compounds of formula (I) wherein $R^1$, $R^2$, $Ar^1$, $Ar^2$, $L^1$ and $L^2$ are as hereinbefore defined and Y is carboxy may be prepared by hydrogenation of compounds of formula (I) wherein $R^1$, $R^2$, $Ar^1$, $Ar^2$, $L^1$, $L^2$ are as hereinbefore defined and Y is a —$CO_2R^{18}$ group (in which $R^{18}$ is benzyl). The reaction may be carried out in the presence of ammonium formate and a suitable metal catalyst, e.g. palladium, supported on an inert carrier such as carbon, preferably in a solvent such as methanol or ethanol and at a temperature at about reflux temperature. The reaction may alternatively be carried out in the presence of a suitable metal catalyst, e.g. platinum or palladium optionally supported on an inert carrier such as carbon, preferably in a solvent such as methanol or ethanol.

Esters of formula (I) wherein $R^1$, $R^2$, $Ar^1$, $Ar^2$, $L^2$ are as hereinbefore defined $L^1$ is a —$R^5$—$R^6$— linkage (in which $R^5$ is as hereinbefore defined and $R^6$ is —C(=O)—$NR^4$—) and Y is a —$CO_2R^{18}$ group (in which $R^{18}$ is as hereinbefore defined) may be prepared by reaction of compounds of formula (VII):

(VII)

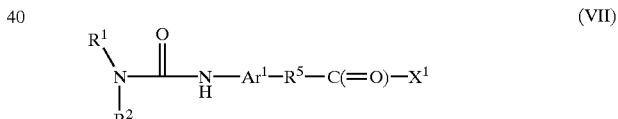

wherein $R^1$, $R^2$, $R^5$ and $Ar^1$ are as hereinbefore and $X^1$ is a hydroxy group or a halogen, preferably chlorine, atom, with amines of formula (VIII):

(VIII)

wherein $R^4$, $R^{18}$, $Ar^2$ and $L^2$ are as hereinbefore defined. When $X^{10}$ is a hydroxy group the reaction may be carried out using standard peptide coupling procedures for example coupling in the presence of O-(7-azabenzotriazol-1-yl)-1,1, 3,3-tetramethyluronium hexafluorophosphate and triethylamine (or diisopropylethylamine) in tetrahydrofuran (or dimethylformamide), at room temperature. When $X^1$ is a halogen atom the acylation reaction may be carried out with the aid of a base, such pyridine, preferably in a solvent such as tetrahydrofuran and at a temperature at about room temperature.

Esters of formula (I) wherein $R^1$, $R^2$, $Ar^1$, $Ar^2$ and $L^2$ are as hereinbefore defined $L^1$ is a —$R^5$—$R^6$— linkage [in which $R^5$ is as hereinbefore defined, and $R^6$ is —$NR^4$—C (=O)— (where $R^4$ is as hereinbefore defined)] and Y is a —$CO_2R^{18}$ group (in which $R^{18}$ is as hereinbefore defined) may be prepared by reaction of compounds of formula (IX):

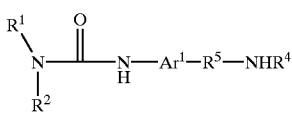

(IX)

wherein $R^1$, $R^2$, $R^4$, $R^5$ and $Ar^1$ are as hereinbefore, with compounds of formula (X):

$$X^2\text{—}C(=O)\text{—}Ar^2\text{—}L^2\text{—}CO_2R^{18} \qquad (X)$$

wherein $R^{18}$, $Ar^2$ and $L^2$ are as hereinbefore defined and $X^2$ is a hydroxy group or a halogen, preferably chlorine, atom, using procedures described hereinbefore for coupling acids or acid halides with amines.

Esters of formula (I) wherein $R^1$, $R^2$, $Ar^1$, $Ar^2$ and $L^2$ are as hereinbefore defined, $L^1$ is a —$R^5$—$R^6$— linkage (in which $R^5$ is as hereinbefore defined and $R^6$ is —O—) and Y is a —$CO_2R^{18}$ group (in which $R^{18}$ is as hereinbefore defined) may be prepared by reaction of compounds of formula (XI):

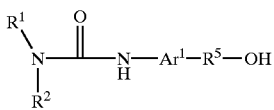

(XI)

wherein $R^1$, $R^2$, $R^5$ and $Ar^2$ are as hereinbefore defined with compounds of formula (XII):

$$HZ^4\text{—}Ar^2\text{—}L^2\text{—}CO_2R^{18} \qquad (XII)$$

wherein $R^{18}$, $Ar^2$ and $L^2$ are as hereinbefore defined and $Z^4$ is O, in the presence of a dialkyl azodicarboxylate, such as diethyl azodicarboxylate, and triphenylphosphine, preferably in a dry ethereal solvent, e.g. diethyl ether or tetrahydrofuran, preferably at or near room temperature.

Alternatively esters of formula (I) wherein $R^1$, $R^2$, $Ar^1$, $Ar^2$ and $L^2$ are as hereinbefore defined, $L^1$ is a —$R^5$—$R^6$— linkage (in which $R^5$ is as hereinbefore defined and $R^6$ is —O—) and Y is a —$CO_2R^{18}$ group (in which $R^{18}$ is as hereinbefore defined) may be prepared by alkylation of compounds of formula (XII), wherein $R^{17}$, $Ar^2$ and $L^2$ are as hereinbefore defined and $Z^4$ is O with the appropriate alkyl bromides of formula (XIII):

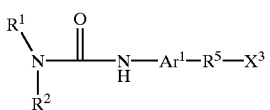

(XIII)

wherein $R^1$, $R^2$, $R^5$ and $Ar^1$ are as hereinbefore defined and $X^3$ is a halogen, preferably bromo, atom using standard alkylation conditions. The alkylation may for example be carried out in the presence of a base, such as an alkali metal carbonate, e.g. potassium carbonate, or alkali metal hydride, e.g. sodium hydride, in dimethylformamide, or dimethyl sulphoxide, at a temperature from about 0° C. to about 100° C.

Esters of formula (I) wherein $R^1$, $R^2$, $Ar^1$, $Ar^2$ and $L^2$ are as hereinbefore defined, $L^1$ is a —$R^5$—$R^6$— linkage (in which $R^5$ is as hereinbefore defined and $R^6$ is —S—) and Y is a —$CO_2R^{18}$ group (in which $R^{18}$ is as hereinbefore defined) may be similarly prepared by alkylation of compounds of formula (XII) wherein $R^{18}$, $Ar^2$ and $L^2$ are as hereinbefore defined and $Z^4$ is S.

Esters of formula (I) wherein $R^1$, $R^2$, $Ar^1$, $Ar^2$, $L^2$ are as hereinbefore defined, $L^1$ is a —$R^5$—$R^6$— linkage [in which $R^5$ is as hereinbefore defined and $R^6$ is —$NR^4$— (where $R^4$ is as hereinbefore defined)] and Y is a —$CO_2R^{18}$ group (in which $R^{18}$ is as hereinbefore defined) may be similarly prepared by alkylation of compounds of formula (VIII), wherein $R^4$, $R^{18}$, $Ar^2$ and $L^2$ are as hereinbefore defined.

Esters of formula (I) wherein $R^1$, $R^2$, $Ar^1$, $Ar^2$ and $L^2$ are as hereinbefore defined, $L^1$ is a —$R^5$—$R^6$— linkage [in which $R^5$ is alkylene and $R^6$ is —C(=O)—] and Y is a —$CO_2R^{18}$ group (in which $R^{18}$ is as hereinbefore defined) may be prepared by reaction of acid chlorides of formula (VII) wherein $R^1$, $R^2$ and $Ar^1$ are as hereinbefore defined, $X^1$ is chloro and $R^5$ is alkylene, with compounds of formula (XIV):

$$Br\text{—}Ar^2\text{—}L^2\text{—}CO_2R^{18} \qquad (XIV)$$

wherein $R^{18}$, $Ar^2$ and $L^2$ are as hereinbefore defined, by the application or adaptation of the methodology described by R. D. Rieke et al, Synth.Commun., 1995, 23, pages 3923–3930.

Esters of formula (I) wherein $R^1$, $R^2$, $Ar^1$, $Ar^2$, $L^2$ are as hereinbefore defined, $L^1$ is a —$R^5$—$R^6$— linkage [in which $R^5$ is as hereinbefore defined and $R^6$ is —$NR^4$—C(=O)—NH— (where $R^4$ is as hereinbefore defined)] and Y is a —$CO_2R^{18}$ group (in which $R^{18}$ is as hereinbefore defined) may be prepared by reaction of compounds of formula (IX) wherein $R^1$, $R^2$, $R^4$, $R^5$ and $Ar^1$ are as hereinbefore defined, with isocyanates of formula (XV):

$$O=C=N\text{—}Ar^2\text{—}L^2\text{—}CO_2R^{18} \qquad (XV)$$

wherein $R^{18}$, $Ar^2$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I) wherein $R^1$, $R^2$, $Ar^1$, $Ar^2$, $L^2$ are as hereinbefore defined, $L^1$ is a —$R^5$—$R^6$— linkage [in which $R^5$ is as hereinbefore defined and $R^6$ is —NH—C(=O)—$NR^4$ (where $R^4$ is as hereinbefore defined)] and Y is a —$CO_2R^{18}$ group (in which $R^{18}$ is as hereinbefore defined) may be similarly prepared by reaction of amines of formula (VIII) wherein $R^4$, $R^{18}$ $Ar^2$ and $L^2$ are as hereinbefore defined with compounds of formula (XVI):

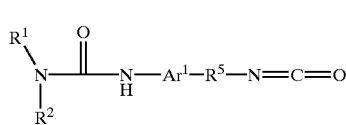

(XVI)

wherein $R^1$, $R^2$, $R^5$ and $Ar^1$ are as hereinbefore defined.

Esters of formula (I) wherein $R^1$, $R^2$, $Ar^1$, $Ar^2$ and $L^2$ are as hereinbefore defined, $L^1$ is a —$R^5$—$R^6$— linkage [in which $R^5$ is as hereinbefore defined and $R^6$ is —$SO_2$—$NR^4$— (where $R^4$ is as hereinbefore defined)] and Y is a —$CO_2R^{18}$ group (in which $R^{18}$ is as hereinbefore defined) may be prepared by reaction of compounds of formula (XVII):

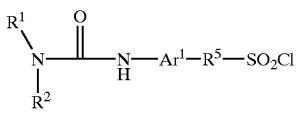

(XVII)

wherein $R^1$, $R^2$, $R^5$ and $Ar^1$ are as hereinbefore defined, with amines of formula (VIII) wherein $R^4$, $R^{18}$ $Ar^2$ and $L^2$ are as hereinbefore defined. The reaction is preferably carried out with the aid of a base, such as a tertiary amine, for example triethylamine, preferably in a solvent such as tetrahydrofuran and at a temperature at about room temperature.

Esters of formula (I) wherein $R^1$, $R^2$, $Ar^1$, $Ar^2$ and $L^2$ are as hereinbefore defined, $L^1$ is a —$R^5$—$R^6$— linkage [in which $R^5$ is as hereinbefore defined and $R^6$ is —$NR^4$—$SO_2$— (where $R^4$ is as hereinbefore defined)] and Y is a —$CO_2R^{18}$ group (in which $R^{18}$ is as hereinbefore defined) may be similarly prepared by reaction of compounds of formula (IX) wherein $R^1$, $R^2$, $R^4$, $R^5$ and $Ar^1$ are as hereinbefore defined with sulphonyl chlorides of formula (XVIII):

$ClSO_2$—$Ar^2$—$L^2$—$CO_2R^{18}$ (XVIII)

wherein $R^{18}$, $Ar^2$ and $L^2$ are as hereinbefore defined.

Esters of formula (I) wherein $R^1$, $R^2$, $Ar^1$, $Ar^2$ and $L^2$ are as hereinbefore defined, $L^1$ is a —$R^5$—$R^6$— linkage [in which $R^5$ is as hereinbefore defined and $R^6$ is —O—C(=O)—] and Y is a —$CO_2R^{18}$ group (where $R^{18}$ is as hereinbefore defined) may be prepared by O-acylation of compounds of formula (XI) wherein $R^1$, $R^2$, $R^5$ and $Ar^1$ are as hereinbefore defined with compounds of formula (X) wherein $R^{18}$, $Ar^2$ and $L^2$ are as hereinbefore defined and $X^2$ is a chlorine atom. The reaction may be carried using standard O-acylation conditions, for example reaction in the presence of a base, such as triethylamine or pyridine, at a temperature from about 0° C. to about room temperature.

Esters of formula (I) wherein $R^1$, $R^2$, $Ar^1$, $Ar^2$ and $L^2$ are as hereinbefore defined, $L^1$ is a —$R^5$—$R^6$— linkage [in which $R^5$ is as hereinbefore defined and $R^6$ is —C(=O)—O—] and Y is a —$CO_2R^{18}$ group (where $R^{18}$ is as hereinbefore defined) may be similarly prepared by O-acylation of compounds of formula (XII) wherein $R^{18}$, $Ar^2$ and $L^2$ are as hereinbefore defined and $Z^4$ is O with compounds of formula (VII) wherein $R^1$, $R^2$, $R^5$ and $Ar^1$ are as hereinbefore defined and $X^1$ is a chlorine atom.

Esters of formula (I) wherein $R^1$, $R^2$, $Ar^1$, $Ar^2$ and $L^2$ are as hereinbefore defined, $L^1$ is a —$R^5$—$R^6$— linkage (in which $R^5$ is as hereinbefore defined and $R^6$ is —O—C(=O)—NH—) and Y is a —$CO_2R^{18}$ group (where $R^{18}$ is as hereinbefore defined) may be prepared by reaction of compounds of formula (XI) wherein $R^1$, $R^2$, $R^5$ and $Ar^1$ are as hereinbefore defined with isocyanates of formula (XV) wherein $R^{18}$, $Ar^2$ and $L^2$ are as hereinbefore defined. The reaction is preferably carried out with the aid of a base, such as a tertiary amine, for example triethylamine, preferably in a solvent such as dichloromethane, and at a temperature at about room temperature.

Esters of formula (I) wherein $R^1$, $R^2$, $Ar^1$, $Ar^2$ and $L^2$ are as hereinbefore defined, $L^1$ is a —$R^5$—$R^6$— linkage (in which $R^5$ is as hereinbefore defined and $R^6$ is —NH—C(=O)—O—] and Y is a —$CO_2R^{18}$ group (where $R^{18}$ is as hereinbefore defined) may be similarly prepared by reaction of isocyanates of formula (XVI) wherein $R^1$, $R^2$, $R^5$ and $Ar^1$ are as hereinbefore defined with compounds of formula (XII) wherein $R^{18}$, $Ar^2$ and $L^2$ are as hereinbefore defined and $Z^4$ is O.

Esters of formula (I) wherein $R^1$, $R^2$, $Ar^1$, $Ar^2$ and $L^2$ are as hereinbefore defined, $L^1$ is a —$R^5$—$R^6$— linkage (in which $R^6$ is a direct bond and $R^5$ is a straight or branched chain $C_{2-6}$alkenylene chain where the carbon—carbon double bond is directly attached to the phenyl ring containing the —$L^2$—$CO_2R^{18}$ group) and Y is a —$CO_2R^{18}$ group (where $R^{18}$ is as hereinbefore defined) may be prepared by reaction of compounds of formula (XIX):

H—C(=O)—$Ar^2$—$L^2$—$CO_2R^{18}$ (XIX)

wherein $R^{18}$, $Ar^2$ and $L^2$ are as hereinbefore defined, with an appropriate phosphorane (or phosphonate ester) of formula (XX):

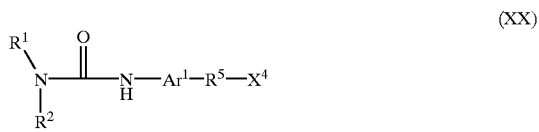

(XX)

wherein $R^1$, $R^2$ and $Ar^1$ are as hereinbefore defined, $R^5$ is a straight or branched chain $C_{1-5}$alkylene chain and $X^4$ is =$PPh_3^+Br^-$ (or —P(=O)(OEt)$_2$), using standard Wiftig (or Horner-Wadsworth-Emmons) coupling procedures (for example those described in Tetrahedron Organic Chemistry Series Volume 11, Organic Synthesis Based On Name Reactions and Unnamed reactions, Editors, J. E. Balwin and P. D. Magnus, pages 181 and 421).

Esters of formula (I), wherein $R^1$, $R^2$, $Ar^1$, $Ar^2$ and $L^1$ are as hereinbefore defined, Y is —$CO_2R^{18}$ (where $R^{18}$ is as hereinbefore defined) and $L^2$ is an alkylene linkage substituted by —$NY^1Y^2$ (in which one of $Y^1$ and $Y^2$ is hydrogen and the other is alkyl, or alkyl substituted by alkoxy, aryl, cyano, cycloalkyl, heteroaryl, heterocycloalkyl, hydroxy, oxo, —$NY^3Y^4$, or one or more —$CO_2R^7$ or —C(=O)—$NY^3Y^4$ groups), may be prepared by reaction of esters of formula (I), wherein $R^1$, $R^2$, $Ar^1$, $Ar^2$ and $L^1$ are as hereinbefore defined, Y is —$CO_2R^{18}$ (where $R^{18}$ is as hereinbefore defined)and $L^2$ is an alkylene linkage substituted by —$NH^2$, with aldehydes of formula (XXI):

$R^{19}$—CHO (XXI)

wherein $R^{19}$ is hydrogen or alkyl, or alkyl substituted by alkoxy, aryl, cyano, cycloalkyl, heteroaryl, heterocycloalkyl, hydroxy, oxo, —$NY^3Y^4$, or one or more —$CO_2R^7$ or —C(=O)—$NY^3Y^4$ groups in the presence of sodium cyanoborohydride. The reaction may be conveniently carried out in methanol, optionally in the presence of sodium acetate and 4 Å molecular sieves, and at a temperature at about room temperature.

Esters of formula (I), wherein $R^1$, $R^2$, $Ar^1$, $Ar^2$ and $L^1$ are as hereinbefore defined, Y is —$CO_2R^{17}$ and $L^2$ contains a —N($R^7$)—C(=O)—$R^8$ group, may be prepared by reaction of amines of formula (I), wherein $R^1$, $R^2$, $Ar^1$, $Ar^2$ and $L^1$ are as hereinbefore defined, Y is —$CO_2R^{18}$ (where $R^{18}$ is as hereinbefore defined) and $L^2$ contains a —NH($R^8$) group, with compounds of formula (XXII):

$R^8$—C(=O)—$X^5$ (XXII)

wherein $R^8$ is as hereinbefore defined and $X^5$ is a hydroxy group or a halogen, preferably chlorine, atom. When $X^5$ is a hydroxy group the reaction may be carried out using standard peptide coupling procedures as described hereinbefore. When $X^5$ is a halogen atom the reaction may be carried out with the aid of a base, such pyridine, preferably in a solvent such as tetrahydrofuran and at a temperature at about room temperature.

Esters of formula (I), wherein $R^1$, $R^2$, $Ar^1$, $Ar^2$ and $L^1$ are as hereinbefore defined Y is —$CO_2R^{18}$ (where $R^{18}$ is as hereinbefore defined) and $L^2$ contains a —$N(R^7)$—C(=O)—$OR^8$ group, may be prepared by reaction of amines of formula (I), wherein $R^1$, $R^2$, $Ar^1$, $Ar^2$ and $L^1$ are as hereinbefore defined, Y is —$CO_2R^{18}$ (where $R^{18}$ is as hereinbefore defined) and $L^2$ contains a —$NH(R^7)$ group, with the appropriate chloroformate, e.g. ethyl (or benzyl) chloroformate compounds, according to standard reaction conditions.

Esters of formula (I), wherein $R^1$, $R^2$, $Ar^1$, $Ar^2$ and $L^1$ are as hereinbefore defined, Y is —$CO_2R^{18}$ (where $R^{18}$ is as hereinbefore defined) and $L^2$ contains a —$N(R^7)$—$SO_2$—$R^8$ group, may be prepared by reaction of amines of formula (I), wherein $R^1$, $R^2$, $Ar^1$, $Ar^2$ and $L^1$ are as hereinbefore defined, Y is —$CO_2R^{18}$ (where $R^{18}$ is as hereinbefore defined) and $L^2$ contains a —$NH(R^7)$ group, with the appropriate sulphonyl chloride, e.g. an aryl(or heteroaryl)sulphonyl chloride, such as phenyl(or pyridyl)sulphonyl chloride, according to standard reaction conditions.

Esters of formula (I), wherein $R^1$, $R^2$, $Ar^1$, $Ar^2$ and $L^1$ are as hereinbefore defined Y is —$CO_2R^{18}$ (in which $R^{18}$ is alkyl) and $L^2$ is a

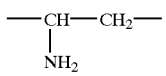

linkage, may be prepared by hydrogenation of esters of formula (I), wherein $R^1$, $R^2$, $Ar^1$, $Ar^2$ and $L^1$ are as hereinbefore defined, Y is —$CO_2R^{18}$ (in which $R^{18}$ is alkyl) and $L^2$ is a

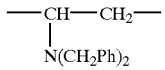

linkage. The reaction may be carried out in the presence of formic acid and a suitable metal catalyst, e.g. palladium, supported on an inert carrier such as carbon, at a temperature at about 60° C. The reaction may conveniently be carried out in the presence of a suitable metal catalyst, e.g. platinum or palladium optionally supported on an inert carrier such as carbon, preferably in a solvent such as methanol or ethanol.

Esters of formula (I), wherein $R^1$, $R^2$, $Ar^1$, $Ar^2$ and $L^1$ are as hereinbefore defined Y is —$CO_2R^{18}$ (in which $R^{18}$ is alkyl) and $L^2$ is a

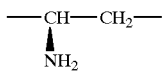

linkage, may be similarly prepared by hydrogenation of esters of formula (I), wherein $R^1$, $R^2$, $Ar^1$, $Ar^2$ and $L^1$ are as hereinbefore defined, Y is —$CO_2R^{18}$ (in which $R^{18}$ is alkyl) and $L^2$ is a

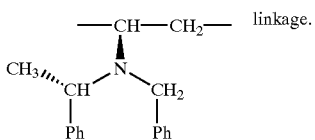 linkage.

Esters of formula (I), wherein $R^1$, $R^2$, $Ar^1$, $Ar^2$ and $L^1$ are as hereinbefore defined Y is —$CO_2R^{18}$ (where $R^{18}$ is as hereinbefore defined) and $L^2$ is a

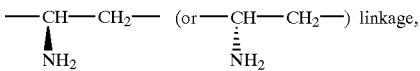

may also be obtained following standard recrystallisation of salts of the racemic mixture, for example recrystallisation of the tartrate salt.

Esters of formula (I), wherein $R^1$, $R^2$, $Ar^1$, $Ar^2$ and $L^1$ are as hereinbefore defined Y is —$CO_2R^{18}$ (where $R^{18}$ is as hereinbefore defined) and $L^2$ is a

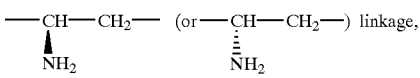

may also be obtained by the application of standard enzymatic resolution procedures for example those described by Soloshonok, V. A., et.al., Tetrahedron: Asymmetry 6 (1995) 7, 1601–1610.

Esters of formula (I) wherein $R^1$, $R^2$, $Ar^1$, $Ar^2$ and $L^1$ are as hereinbefore defined Y is —$CO_2R^{18}$ (where $R^{18}$ is as hereinbefore defined) and $L^2$ is a

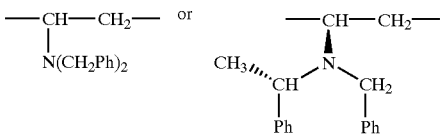

linkage, may be prepared by reaction of compounds of formula (XXIII):

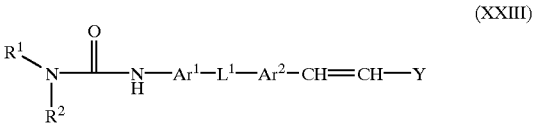

(XXIII)

wherein $R^1$, $R^2$, $Ar^1$, $Ar^2$ and $L^1$ are as hereinbefore defined and Y is —$CO_2R^{18}$ (where $R^{18}$ is as hereinbefore defined), with an alkali metal hydride, such as sodium hydride, in an inert solvent, e.g. tetrahydrofuran, and at a temperature at about room temperature, and subsequent reaction with the anion derived from treating dibenzylamine, or (S)-N-benzyl-α-methylbenzylamine, with butyllithium, at a temperature at about −78° C.

Lactones of formula (I) wherein $R^1$, $R^2$, $Ar^1$, $Ar^2$ and $L^1$ are as hereinbefore defined and the moiety —$L^2$—Y is 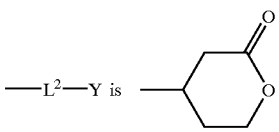

may be prepared by the selective reduction (using for example a borane derivative or lithium borohydride) of compounds of formula (I) wherein $R^1$, $R^2$, $Ar^1$, $Ar^2$ and $L^1$ are as hereinbefore defined and the moiety

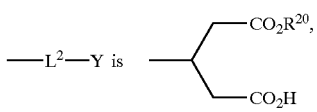

in which $R^{20}$ is lower alkyl, followed by spontaneous cyclisation of the intermediate hydroxy compound. The reduction can be achieved by the application or adaptation of the procedures described by C. J. Francis and J. Bryan Jones, J. Chem. Soc, Chem. Commun., 1984, (9), 579–58, J.Hiratake et al, J. Chem. Soc, Perkin Trans, 1987, 1 (5), 1053–8 or L. K. P. Lam et al, J. Org. Chem. (1986), 51(11), 2047–50.

Lactones of formula (I) wherein $R^1$, $R^2$, $Ar^1$, $Ar^2$ and $L^1$ are as hereinbefore defined and the moiety

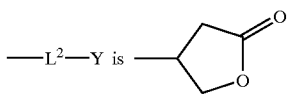

may be similarly prepared from compounds of formula (I) wherein $R^1$, $R^2$, $Ar^1$, $Ar^2$ and $L^1$ are as hereinbefore defined and the moiety

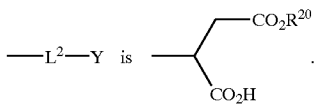

According to a further feature of the present invention, compounds of the invention may be prepared by interconversion of other compounds of the invention.

For example compounds of formula (I) wherein $R^1$, $R^2$, $Ar^1$, $Ar^2$, $L^1$ and $L^2$ are as hereinbefore defined and Y is —C(=O)—NHOH, may be prepared by reaction of compounds of formula (I) wherein $R^1$, $R^2$, $Ar^1$, $Ar^2$, $L^1$ and $L^2$ are as hereinbefore defined and Y is carboxy, with hydroxylamine using standard peptide coupling procedures such as treatment with a carbodiimide, for example dicyclohexylcarbodiimide, in the presence of triethylamine, in an inert solvent such as dichloromethane or tetrahydrofuran and at a temperature at about room temperature. The coupling may also be carried out using 1-hydroxybenzotriazole and 1-(3-dimethylaminopropyl)-3-ethylcarbodiimide in dichloromethane at room temperature. The preparation may also be carried out using an O-protected hydroxylamine such as O-(trimethylsilyl)hydroxylamine, O-(t-butyldimethylsilyl)-hydroxylamine, or O-(tetrahydropyranyl)hydroxylamine followed by treatment with acid.

As another example of the interconversion process, compounds of formula (I) wherein $R^1$, $R^2$, $Ar^1$, $Ar^2$, $L^1$ and Y are as hereinbefore defined and $L^2$ is an optionally substituted alkylene linkage, may be prepared by hydrogenation of the corresponding compounds of formula (I) in which $L^2$ is the corresponding optionally substituted alkenylene linkage. The hydrogenation may be carried out using hydrogen (optionally under pressure) in the presence of a suitable metal catalyst, e.g. platinum or palladium optionally supported on an inert carrier such as carbon, preferably in a solvent such as methanol or ethanol, and at a temperature at about room temperature.

As another example of the interconversion process, compounds of formula (I) wherein $R^1$, $R^2$, $Ar^1$, $Ar^2$, $L^2$ and Y are as hereinbefore described and $L^1$ is a —$R^5$—$R^6$— linkage where $R^5$ is a straight or branched chain $C_{2-6}$alkylene chain and $R^6$ is a direct bond, may be similarly prepared by hydrogenation of the corresponding compounds of formula (I) in which $L^1$ is a —$R^5$—$R^6$— linkage where $R^5$ is a straight or branched chain $C_{2-6}$alkenylene chain and $R^6$ is a direct bond.

As another example of the interconversion process, compounds of the invention containing a heterocyclic group wherein the hetero atom is a nitrogen atom may be oxidised to their corresponding N-oxides. The oxidation may conveniently be carried out by means of reaction with a mixture of hydrogen peroxide and an organic acid, e.g. acetic acid, preferably at or above room temperature, for example at a temperature of about 60–90° C. Alternatively, the oxidation may be carried out by reaction with a peracid, for example peracetic acid or m-chloroperoxybenzoic acid, in an inert solvent such as chloroform or dichloromethane, at a temperature from about room temperature to reflux, preferably at elevated temperature. The oxidation may alternatively be carried out by reaction with hydrogen peroxide in the presence of sodium tungstate at temperatures between room temperature and about 60° C.

It will be appreciated that compounds of the present invention may contain asymmetric centres. These asymmetric centres may independently be in either the R or S configuration. It will be apparent to those skilled in the art that certain compounds of the invention may also exhibit geometrical isomerism.

It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Reference Examples or their obvious chemical equivalents.

Acids of formula (II) wherein $R^4$, $R^{17}$, $Ar^2$ and $L^2$ are as hereinbefore defined may be prepared from the corresponding esters by acid or alkaline hydrolysis of the corresponding esters (XXIV) wherein $R^4$, $R^{17}$, $R^{18}$, $Ar^2$ and $L^2$ are as hereinbefore defined using conditions described hereinbefore.

Acid chlorides of formula (VII) wherein $R^1$, $R^2$, $R^5$ and $Ar^1$ are as hereinbefore defined and $X^1$ is a chlorine atom may be prepared from the corresponding acids of formula (VII) wherein $R^1$, $R^2$, $R^5$ and $Ar^1$ are as hereinbefore defined and $X^1$ is hydroxy, by the application of standard procedures for the conversion of acids to acid chlorides for example by reaction with oxalyl chloride.

Acid chlorides of formula (X) wherein $R^{18}$, $Ar^2$ and $L^2$ are as hereinbefore defined and $X^2$ is a chlorine atom may be similarly prepared from the corresponding acids of formula (X) wherein $R^{18}$, $Ar^2$ and $L^2$ are as hereinbefore defined and $X^2$ is hydroxy.

Compounds of formula (IX) wherein $R^1$, $R^2$, $R^5$ and $Ar^1$ are as hereinbefore defined and $R^4$ is methyl may be prepared by treatment of the corresponding compounds of formula (IX) wherein $R^1$, $R^2$, $R^5$ and $Ar^1$ are as hereinbefore defined and $R^4$ is hydrogen with formic acetic anhydride followed by reduction with lithium aluminium hydride according to the procedure described by L. G. Humber L G et al, J Med Chem, 1971, 14, page 982.

Compounds of formula (VIII) wherein $R^{18}$, $R^4$, $Ar^2$ and $L^2$ are as hereinbefore defined may be prepared by reaction of compounds of formula (XXIV):

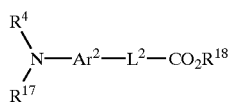

(XXIV)

wherein $R^4$, $R^{18}$, $Ar^2$ and $L^2$ are as hereinbefore defined and $R^{17}$ is an acid-labile protecting group, such as benzyloxycarbonyl, with trifluoroacetic acid, in an inert solvent, such as dichloromethane and at a temperature at about room temperature. This method is particularly suitable for the preparation of compounds of formula (VIII) where $R^4$ is methyl.

Compounds of formula (VIII) wherein $R^{18}$, $Ar^2$ and $L^2$ are as hereinbefore defined and $R^4$ is hydrogen may be prepared by reduction of the corresponding nitro compounds of formula (XXV):

$O_2N$—$Ar^2$—$L^2$—$CO_2R^{18}$ (XXV)

wherein $R^{18}$, $Ar^2$ and $L^2$ are as hereinbefore defined. The reduction may be carried out using iron powder and ammonium chloride, in aqueous ethanol at a temperature at about reflux.

Compounds of formula (VIII) wherein $R^{18}$ and $Ar^2$ are as hereinbefore defined and $R^4$ is hydrogen and $L^2$ is alkylene (e.g. —$CH(CH_3)$—$CH_2$—) may be prepared by reduction of the corresponding nitro compounds of formula (XXV) wherein $R^{18}$ and $Ar^2$ as hereinbefore defined and $L^2$ is the corresponding alkenylene chain (e.g. —$CH(CH_3)$=$CH_2$—). The reduction may be carried out by hydrogenation using standard conditions, for example those described hereinbefore.

Compounds of formula (IX) wherein $R^1$, $R^2$, $R^5$ and $Ar^1$ are as hereinbefore defined and $R^4$ is hydrogen may be prepared by reaction of compounds of formula (XIII) wherein $R^1$, $R^2$, $R^5$ and $Ar^1$ are as hereinbefore defined and $X^3$ is bromo with phthalimide potassium salt in dimethylformamide followed by reaction with hydrazine hydrate in ethanol (for example using the conditions described by O. Diouf et al., Heterocycles, 1995, 41, page 1219–1233).

Compounds of formula (XI) wherein $R^1$, $R^2$, $R^5$ and $Ar^1$ are as hereinbefore defined and $R^5$ is methylene (or a $C_{2-6}$ straight or branched alkylene chain), may be prepared by reduction of esters of formula (XXVI):

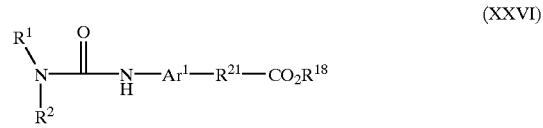

(XXVI)

wherein $R^1$, $R^2$ and $Ar^1$ are as hereinbefore defined, $R^{18}$ is alkyl and $R^{21}$ is a direct bond (or a $C_{1-5}$ straight or branched alkylene chain). The reduction may conveniently be carried out with diisobutylaluminium hydride in an inert solvent, such as tetrahydrofuran, at a temperature from about −78° C. to about room temperature. The reduction may also be carried out with lithium aluminium hydride in an inert solvent, such as an ether, for example diethyl ether, at a temperature from about room temperature to about reflux.

Compounds of formula (XII) wherein $R^{18}$, $Ar^2$ and $L^2$ are as hereinbefore defined and $Z^4$ is O may be prepared from the corresponding acids of formula (XXVII):

$HZ^4$—$Ar^2$—$L^2$—$CO_2H$ (XXVII)

wherein $Ar^2$ and $L^2$ are as hereinbefore defined and $Z^4$ is O, by standard esterification procedures for example reaction with a lower alkyl alcohol (e.g. methanol) in the presence of an acid catalyst, such as hydrogen chloride or sulphuric acid.

Compounds of formula (XII) wherein $R^1$, $R^2$ and $Ar^1$ are as hereinbefore defined, $R^5$ is an alkylene chain and $X^3$ is bromo may be prepared by reaction of compounds of formula (XI) wherein $R^1$, $R^2$ and $Ar^1$ are as hereinbefore defined, $R^5$ is an alkylene chain with phosphorus tribromide in an inert solvent such as carbon tetrachloride and at a temperature at about room temperature.

Compounds of formula (XV) wherein $R^{18}$, $Ar^2$ and $L^2$ are as hereinbefore defined may be prepared from compounds of formula (VIII) wherein $R^{18}$, $Ar^2$ and $L^2$ are as hereinbefore defined and $R^4$ is hydrogen with phosgene following standard reaction conditions for the conversion of amines to isocyanates.

Compounds of formula (XVI) wherein $R^1$, $R^2$, $R^5$ and $Ar^1$ are as hereinbefore defined may be similarly prepared from compounds of formula (IX) wherein $R^1$, $R^2$, $R^5$ and $Ar^1$ are as hereinbefore defined and $R^4$ is hydrogen.

Compounds of formula (XVII) wherein $R^1$, $R^2$, $R^5$ and $Ar^1$ are as hereinbefore defined may be prepared from compounds of formula (XIII) wherein $R^1$, $R^2$, $R^5$ and $Ar^1$ are as hereinbefore defined and $X^3$ is bromo by reaction with sodium sulphite followed by phosphorus trichloride according to the described by P. N. Culshaw and J. C. Walton, J.Chem Soc, Perkin Trans II, 1991, 8, pages1201–1208.

Compounds of formula (XVIII) wherein $R^{18}$, $Ar^2$ and $L^2$ are as hereinbefore defined may be prepared from compounds of formula (VIII) wherein $R^{18}$, $Ar^2$ and $L^2$ are as hereinbefore defined and $R^4$ is hydrogen by application or adaptation of the procedures described by J. A. Diaz and S. Vega J.Heterocycl.Chem., 1994, 31, pages 93–96 for the conversion of aminopyrazoles to the corresponding pyrazolylsulphonyl chlorides.

Compounds of formula (XX) wherein $R^1$, $R^2$ and $Ar^1$ are as hereinbefore defined, $R^5$ is a straight or branched chain $C_{1-5}$alkylene chain and $X^4$ is $=PPh_3{}^+Br^-$ may be prepared by reaction of compounds of formula (XIII) wherein $R^1$, $R^2$ and $Ar^1$ are as hereinbefore defined, $R^5$ is a straight or branched chain $C_{1-5}$alkylene chain and $X^3$ is a bromine atom by reaction with triphenylphosphine in an inert solvent and at a temperature from about room temperature to about reflux temperature of the solvent.

Compounds of formula (XXV) wherein $Ar^2$ is as defined hereinbefore, $R^{18}$ is alkyl and $L^2$ is $-C(R^{22})=C(R^{23})-$ (in which $R^{22}$ and $R^{23}$ are independently hydrogen or alkyl) may be prepared by reaction of compounds of formula (XXVIII):

$$O_2N-Ar^2-C(=O)-R^{22} \quad\quad (XXVIII)$$

wherein $Ar^2$ is as hereinbefore defined and $R^{22}$ is hydrogen or alkyl, with a dialkylphosphonoacetate of formula (XXIX)_:

$$(R^{24}O)_2P(=O)-CH(R^{23})-CO_2R^{18} \quad\quad (XXIX)$$

wherein $R^{18}$ is as hereinbefore defined, $R^{23}$ is hydrogen or alkyl and $R^{24}$ is a $C_{1-4}$alkyl group, in the presence of a base such as an alkali metal alkoxide (for example potassium t-butoxide), or an alkali metal hydride (for example sodium hydride). The reaction is preferably carried out in a solvent such as dimethylformamide or tetrahydrofuran. This methodology is particularly suitable for the preparation of compounds of formula (XXIV) wherein $Ar^2$ is pyridindiyl.

Acids of formula (XXVII) wherein $Ar^2$ and $L^2$ are as hereinbefore defined and $Z^4$ is O may be prepared by the application or adaptation of procedures described by A. G. Meyers and J. L. Gleason, J.Org.Chem., 1996, 61, pages 813–815. This methodology is particularly suitable for compounds where $Ar^2$ is pyridindiyl.

Acids of formula (XXVII) wherein $Ar^2$ and $L^2$ are as hereinbefore defined and $Z^4$ is O may also be prepared by the application or adaptation of procedures described by S. R. Schow et al, J.Org.Chem., 1994, 59, pages 6850–6852. This methodology is particularly suitable for compounds where $Ar^2$ is pyridindiyl.

Intermediates of formulae (Resin 1), (Resin 2), (Resin 3), (Resin 4) and (Resin 5) are novel compounds and, as such, they and their processes described herein for their preparation constitute further features of the present invention.

The present invention is further Exemplified but not limited by the following illustrative Examples and Reference Examples.

High Pressure Liquid Chromatography (HPLC) conditions for determination of retention times (RT) were: 15 cm Hypersil Elite C-18 column, ELS detector; solvent acetonitrile/water gradient (both buffered with 0.5% trifluoroacetic acid): 20% acetonitrile for 3 minutes; than ramp up to 80% over the next 12 minutes; maintain at 80% acetonitrile for 3 minutes; then ramp back to 20% acetonitrile over 0.5 minutes (total run time 20 minutes).

EXAMPLE 1

3-[4-(2-{4-[(2,3-Dihydro-indole-1-carbonyl)-amino]-3-methoxy-phenyl}-acetylamino)-2-pyridyl]-propionic acid Step 1. HMBA-AM resin (Novabiochem, 0.83 mmol/g, 4 g) was swelled with dimethylformamide (about 7 ml) and the treated with a solution of 3-[4-(N-Boc{amino})-2-pyridyl]propionic acid (1.3 g) and O-(7-azabenzotriazol-1-yl)-1,1,3,3-tetramethyluronium hexafluorophosphate (1.9 g) in dimethylformamide (about 20 ml), followed by diisopropylethylamine (2.7 ml). After shaking gently at room temperature overnight the resin was rained then washed (i) three times with dimethylformamide, (ii) three times with tetrahydrofuran, (iii) twice with dichloromethane, (iii) twice with cyclohexane, (iii) twice with dichloromethane and then dried under vacuum.

Step 2. The resin from Step 1 (40 mg) was treated with a mixture of trifluoroacetic acid and dichloromethane (1:1, 1 ml) at room temperature for about 1 hour. The resin was drained and then washed thoroughly with dichloromethane, then three times with dimethylformamide.

Step 3. The resin from Step 2 was suspended in dimethylformamide (1 ml) then treated with a solution of 4-(N-{Boc}amino)-3-methoxyphenylacetic acid (20 mg) and O-(7-azabenzotriazol-1-yl)-1,1,3,3-tetramethyluronium hexafluorophosphate in dimethylformamide (0.5 ml), followed by diisopropylethylamine (35 µL) and kept at room temperature for 1 hour. The resin was drained and then washed (i) three times with dimethylformamide, (ii) three times with tetrahydrofuran, (iii) three times with dichloromethane and then dried.

Step 4. The resin from Step 3 was treated with a mixture of trifluoroacetic acid/dichloromethane (1:1, 1 ml) at room temperature for about 1 hour. The resin was drained and washed thoroughly with dichloromethane, then re-suspended in fresh dichloromethane (1 ml). This suspension was treated with a solution of 4-nitrophenylchloroformate (67 mg) in a mixture of dichloromethane and tetrahydrofuran (1:1 by volume, 1 ml), followed by diisopropylethylamine (58 µL). After 1 hour at room temperature the resin was drained and then washed (i) six times with dichloromethane, (ii) three times with dimethylformamide.

Step 5. The resin from Step 4 was suspended in dimethylformamide (1 ml) then treated with indoline (40 µL), followed by triethylamine (100 ml). After standing at room temperature for 1 hour the resin was drained, then washed (i) three times with dimethylformamide, (ii) three times with tetrahydrofuran, (iii) three times with dichloromethane and then dried under vacuum.

Step 6. The resin from Step 5 was treated with a mixture of tetrahydrofuran, methanol and 1.0M aqueous sodium hydroxide (7:3:1 by volume, 1 ml) and the mixture kept at room temperature for 1–2 hours. The resin was drained then washed with a mixture of tetrahydrofuran, methanol and 1.0M aqueous sodium hydroxide (7:3:1 by volume, 1 ml). The combined washings and filtrate was allowed to stand at room temperature overnight then acidified by the addition of a few drops of acetic acid, then evaporated to give the title compound.

EXAMPLE 2

(a) 3-[4-(2-{4-[(2,3-Dihydro-indole-1-carbonyl)-amino]-3-methoxy-phenyl}-acetylamino)-phenyl]-butyric acid A solution of tert-butyl 3-[4-(2-{4-[(2,3-dihydro-indole-1-carbonyl)-amino]-3-methoxy-phenyl}-acetylamino)- phenyl]-butyrate [580 mg, Reference Example 1(a)] in dichloromethane (20 ml) was treated with treated with trifluoroacetic acid (1 ml). After 2 hours at room temperature further (1 ml) trifluoroacetic acid was added and the solution was then kept at room temperature overnight. The reaction mixture was evaporated and the residue was suspended in water. This suspension was treated with 1.0 M sodium hydroxide solution (5 ml) and then washed twice with ethyl acetate, then acidified to pH 1 with hydrochloric acid and then filtered. The resultant white solid was washed with water then dried to give the title compound (450 mg) as a white powder, m.p. 152–154° C. [Elemental analysis: C, 67.35; H, 6.02; N, 8.46%. Calculated for $C_{28}H_{29}N_3O_5$.0.63$H_2O$: C, 67.41; H, 6.11; N, 8.42%].

(b) By proceeding in a similar manner but using tert-butyl 3-[4-({(N-methyl-N-phenyl)amino}carbonyl)-amino]-3-methoxy-phenyl}-acetylamino)-phenyl]-butyrate [Reference Example 1(b)] there was prepared 3-[4-({(N-methyl-N-phenyl)amino}carbonyl)-amino)-3-methoxy-phenyl}-acetylamino)-phenyl]-butyric acid as a yellow-brown foam. HPLC: $R_T$=14.6 minutes. MS (ES positive): 474 (MH$^-$).

EXAMPLE 3

(R/S) 3-Benzoylamino-3-[4-(2-{4-[(2,3-dihydro-indole-1-carbonyl)-amino]-phenyl}-acetylamino)-phenyl]-propionic acid Step 1. Bromo-Wang resin (Novabiochem, loading 1.0 mmol/g, 6.9 g) was suspended in the minimum volume of dimethylformamide (about 25 ml), then treated successively with (R/S) 3-(N-Fmoc-amino)-3-(4-nitrophenyl)propionic acid (3.7 g), cesium iodide (1.8 g) and diisopropylethylamine (1.5 ml). The mixture was gently agitated at room temperature overnight. The resin was drained then washed (i) five times with dimethylformamide, (ii) twice with methanol, (iii) three times with tetrahydrofuran, (iv) 35 methanol, (v) dichloromethane;

Step 2. The resin from step 1 was treated with a 20% solution of piperidine in dimethylformamide at room temperature for 2 hours. The resin was drained then washed (i) three times with dimethylformamide, (ii) methanol, (iii) tetrahydrofuran, (iv) methanol, (v) dichloromethane and then dried under vacuum. An NMR loading test gave 0.61 mmol/g of the required material (theoretical=0.88 mmol/g).

Step 3. A portion of the resin from Step 2 (615 mg, equivalent to 0.55 mmol) was swelled in dimethylformamide (2 ml) and then treated successively with a solution of O-(7-azabenzotriazol-1-yl)-1,1,3,3-tetramethyluronium hexafluorophosphate (630 mg) and benzoic acid (200 mg) in dimethylformamide (1 ml), followed by diisopropylethylamine (0.58 ml). The mixture was allowed to stand at room temperature for 4 hours with occasional shaking. The resin was drained then washed (i) four times with dimethylformamide, (ii) methanol, (iii) tetrahydrofuran, (iv) methanol, (v) dichloromethane, (vi) ether and then dried under vacuum.

Step 4. A portion of the resin from Step 32 (300 mg) was treated with a 2M solution of tin (2) chloride in dimethylformamide (3 to 4 ml). The mixture was allowed to stand at room temperature with occasional shaking for 7 hours. The resin was drained then washed (i) three times with dimethylformamide, (ii) twice with methanol, (iii) twice with tetrahydrofuran, (iv) twice with methanol and (v) twice with dichloromethane.

Step 5. The resin from Step 4 was suspended in dimethylformamide (5 ml) and then treated with a solution of O-(7-azabenzotriazol-1-yl)-1,1,3,3-tetramethyluronium hexafluorophosphate (350 mg) and 4-(-Fmoc-amino) phenylacetic acid (240 mg) in dimethylformamide (2 ml), followed by diisopropylethylamine (0.32 ml). After standing at room temperature for 4 hours the resin was drained and then washed (i) with dimethylformamide, (ii) with methanol, (iii) with tetrahydrofuran, (iv) with methanol and (v) with dichloromethane.

Step 6. The resin from Step 5 was suspended in dichloromethane (5 ml) then treated with diisopropylethylamine (0.52 ml) followed, cautiously and in small portions, by triphosgene (270 mg). After standing for 1–2 hours the resin was drained, washed with dichloromethane, and then re-suspended in fresh dichloromethane. Pyridine (0.25 ml) was added, followed by indoline (0.34 ml) and the mixture was allowed to stand at room temperature overnight. The resin was drained and washed thoroughly (i) with dichloromethane, (i) with dimethylformamide, (ii) with methanol, (iii) with tetrahydrofuran, (iv) with methanol and (v) with dichloromethane.

Step 7. The resin from Step 6 was treated with a mixture of trifluoroacetic acid/dichloromethane (1:1 by volume) at room temperature for 1 hour. The mixture was filtered and the filtrate was evaporated. The residual dark oil was triturated with a mixture of dichloromethane and ether to give (R/S) 3-benzoylamino-3-[4-(2-{4-[(2,3-dihydro-indole-1-carbonyl)-amino]-phenyl}-acetylamino)-phenyl]-propionic acid (43 mg) as a pink solid. HPLC: $R_T$=14.2 minutes. MS (ES): 561(MH$^-$).

EXAMPLE 4

(a) (R/S) 3-acetylamino-3-[4-(2-{4-[(2,3-dihydro-indole-1-carbonyl)-amino-phenyl}-acetylamino)-phenyl]-propionic acid Step 1. HMBA-AM resin (Novabiochem, 0.83 mmol/g, 4 g) was swelled with dimethylformamide (about 7 ml) and to this was added a solution of (R/S) 3-acetyl-amino-3-[4-(N-Boc{amino})-phenyl]-propionic acid (1.6 g) and O-(7-azabenzotriazol-1-yl)-1,1,3,3-tetramethyluronium hexafluorophosphate (1.9 g) in dimethylformamide (about 20 ml), followed by diisopropylethylamine (2.7 ml). The mixture was gently shaken at room temperature overnight. The resin was drained, then washed (i) three with dimethylformamide, (ii) three times with tetrahydrofuran, (iii) twice with dichloromethane, (iv) twice with cyclohexane, (v) twice with dichloromethane and then dried under vacuum.

Step 2. The resin from Step 1 (40 mg) was treated with a mixture of trifluoroacetic acid/dichloromethane (1:1, 1 ml) at room temperature for about 1 hour then drained and then washed thoroughly (i) with dichloromethane, (ii) three times with dimethylformamide.

Step 3. The resin from Step 2 was suspended in dimethylformamide (1 ml), treated with a solution of 4-(N-{Boc}amino)phenylacetic acid (20 mg) and O-(7-azabenzotriazol-1-yl)-1,1,3,3-tetramethyluronium hexafluorophosphate in dimethylformamide (0.5 ml), followed by diisopropylethylamine (35 µL) and kept at room temperature for 1 hour. The resin was drained, then washed (i) three times with dimethylformamide, (ii) three times with tetrahydrofuran, (iii) three times with dichloromethane and then dried.

Step 4. The resin from Step 3 was treated with a mixture of trifluoroacetic acid/dichloromethane (1:1, 1 ml) at room temperature for about 1 hour, then drained and then washed thoroughly with dichloromethane.

Step 5. The resin from Step 4 was suspended in dichloromethane (1 ml) then treated with diisopropylethylamine (60 μL) and then with triphosgene (30 mg). After 1–2 hours at room temperature for 1–2 hours the resin was drained and then washed thoroughly with dichloromethane.

Step 6. The resin from Step 5 was suspended in dichloromethane (1 ml) then treated with pyridine (30 μL) followed by indoline. After 1–2 hours at room temperature the resin was drained, then washed (i) three times with dichloromethane, (ii) three times with tetrahydrofuran, (iii) three times with dimethylformamide, (iv) three times with tetrahydrofuran, (v) three times with dichloromethane and then dried under vacuum.

Step 7. The resin from Step 6 was treated with a mixture of tetrahydrofuran, methanol and 1.0M aqueous sodium hydroxide (7:3:1 by volume, 1 ml) and the mixtures kept at room temperature for 1–2 hours. The resin was drained, then washed with a mixture of tetrahydrofuran, methanol and 1.0M aqueous sodium hydroxide (7:3:1 by volume, 1 ml). The combined filtrate and washings was allowed to stand at room temperature overnight then acidified by the addition of a few drops of acetic acid and then evaporated to give (R/S) 3-acetylamino-3-[4-(2-{4-[(2,3-dihydro-indole-1-carbonyl)-amino]-phenyl}-acetylamino)-phenyl]-propionic acid.

(b) By proceeding in a similar manner but using 4-(N-{Boc}amino)-3-methoxyphenylacetic acid in Step 3 there was prepared (R/S) 3-acetylamino-3-[4-(2-{4-[(2,3-dihydro-indole-1-carbonyl)-amino]-3-methoxyphenyl}-acetylamino)-phenyl]-propionic acid.

(c) By proceeding in a similar manner but using 4-(N-{Boc}amino)-3-methoxyphenylacetic acid in Step 3 and using (R/S) N-methyl-N-(1-phenylethyl)amine in Step 6 there was prepared (R/S) 3-acetylamino-3-[4-({N-methyl-N-(1-phenylethyl)amino}carbonyl)-amino]-3-methoxy-phenyl}-acetylamino)-phenyl]-propionic acid.

(d) By proceeding in a similar manner but using 4-(N-{Boc}amino)-3-methoxyphenylacetic acid in Step 3 and using N-(methyl)benzylamine in Step 6 there was prepared (R/S) 3-acetylamino-3-[4-({N-benzyl-N-methyl-amino}carbonyl)-amino]-3-methoxyphenyl}-acetylamino)-phenyl]-propionic acid.

EXAMPLE 5

(a) (R) 3-[4-(2-{4-[(2,3-Dihydro-indole-1-carbonyl)-amino]-3-methoxy-phenyl}-acetylamino)-phenyl]-butyric acid A suspension of ethyl (R) 3-[4-(2-{4-[(2,3-dihydro-indole-1-carbonyl)-amino]-3-methoxy-phenyl}-acetylamino)-phenyl]-butyrate (1.3 g, Reference Example 4) in ethanol (40 mL) and water (15 mL) was treated with sodium hydroxide (5 mL, 1M). After stirring at 50° C. for 3 hours the mixture was evaporated to low bulk and then acidified with hydrochloric acid (1M). The resulting white precipitate was filtered, then washed with water, then with ether, and then dried to give the title compound (1.06 g) as a white powder. HPLC: $R_T$=15.3 minutes (>95% by ELS). MS(ES$^+$): 488(MH$^+$); MS(ES$^-$): 486(M$^-$).

(b) By proceeding in a similar manner to Example 5(a) but using methyl (R) 3-[4-(2-{4-[(2,3-dihydro-indole-1-carbonyl)-amino]-3-methoxy-phenyl}-acetylamino)-phenyl]-3-[(5-methyl-isoxazole-3-carbonyl)-amino]-propionate [Reference Example4(b)] there was prepared (R) 3-[4-(2-{4-[(2,3-dihydro-indole-1-carbonyl)-amino]-3-methoxy-phenyl}-acetylamino)-phenyl]-3-[(5-methyl-isoxazole-3-carbonyl)-amino]-propionic acid as a white powder. HPLC: $R_T$=14.9 minutes (97% by ELS). MS(ES$^+$): 598 (MH$^+$).

REFERENCE EXAMPLE 1

(a) tert-Butyl 3-[4-(2-{4-[(2,3-dihydro-indole-1-carbonyl)-amino]-3-methoxy-phenyl}-acetylamino)-phenyl]-butyrate Triphosgene (150 mg) was added to a stirred solution of tert-butyl 3-[4-({4-amino-3-methoxyphenyl}acetylamino)phenyl]butyrate (540 mg, Reference Example 2) in dichloromethane (50 ml) at 0–5° C. under an atmosphere of nitrogen. After stirring for one hour the mixture was treated with a solution of indoline (0.15 ml) in dichloromethane (2.5 ml) and triethylamine (0.51 ml). This mixture was allowed to stand at room temperature overnight and then evaporated. The residual gummy solid was suspended in water and the suspension was acidified to pH 1 by addition of hydrochloric acid. The resulting pale green solid was filtered and then subjected to flash chromatography on silica eluting with 0.2% to 1% methanol in dichloromethane to give the title compound (580 mg) as an off-white solid.

(b) By proceeding in a similar manner to Reference Example 1 but using N-methylaniline to replace the indoline there was prepared tert-butyl 3-[4-({(N-methyl-N-phenyl)amino}carbonyl)-amino]-3-methoxy-phenyl}-acetylamino)-phenyl]-butyrate.

REFERENCE EXAMPLE 2 tert-Butyl 3-[4-({4-amino-3-methoxyphenyl}acetylamino)phenyl]butyrate

A solution of tert-butyl 3-[4-({3-methoxy-4-nitrophenyl}acetylamino)phenyl]-butyrate (3.83 g, Reference Example 3) in ethyl acetate (100 ml) was treated with 5% palladium on charcoal. This mixture was hydrogenated at room temperature and pressure. The catalyst was removed by filtration, and the filtrate was evaporated to give the title compound (3.24 g) as a pale green solid.

REFERENCE EXAMPLE 3 tert-Butyl 3-[4-({3-methoxy-4-nitrophenyl}acetylamino)phenyl]butyrate

A solution of (3-methoxy-4-nitro)phenylacetyl chloride (2.8 g) in dichloromethane (50 ml) was treated with tert-butyl (4-aminophenyl)butyrate (2.9 g) followed by triethylamine (1.9 ml). After standing at room temperature overnight the reaction mixture was washed with water, then with 5% potassium carbonate solution, then dried over sodium sulphate and then evaporated. The residue was recrystallised from toluene to give the title compound (3.8 g) as a white solid.

REFERENCE EXAMPLE 4

(a) Ethyl (R) 3-[4-(2-{4-[(2,3-dihydro-indole-1-carbonyl)-amino]-3-methoxy-phenyl}-acetylamino)-phenyl]-butyrate A solution of ethyl (R) 3-(4-aminophenyl)butyrate (790 mg), 4-[(2,3-dihydro-indole-1-carbonyl)-amino]-3-methoxy-phenyl-acetic acid (1.24 g, Reference Example 5) and O-(7-azabenzotriazol-1-yl)-1,1,3,3-tetramethyluronium hexafluorophosphate (1.45 g) in dimethylformamide (20 mL) was treated in one portion with diisopropylethylamine (1.4 mL). The resulting mixture was stirred at room temperature for 2 hours then poured into water (100 mL) and then extracted three times with ethyl acetate (50 mL). The combined extracts were washed with hydrochloric acid (0.5M), then with sodium hydrogen carbonate solution, then dried and then evaporated. The residue was triturated with a mixture of ethyl acetate and petrol to give the title compound (1.7 g) as a pink/orange powder. HPLC: $R_T$=18.9 minutes (86% by ELS).

(b) By proceeding in a similar manner to Reference Example 4(a) but using methyl (R) 3-(4-aminophenyl)-3-[(5-methyl-isoxazole-3-carbonyl)-amino]-propionate there was prepared methyl (R) 3-[4-(2-{4-[(2,3-dihydro-indole-1-carbonyl)-amino]-3-methoxy-phenyl}-acetylamino)-phenyl]-3-[(5-methyl-isoxazole-3-carbonyl)-amino]-propionate as a white powder. HPLC: $R_T$=16.9 minutes (90% by ELS).

REFERENCE EXAMPLE 5

4-[(2,3-dihydro-indole-1-carbonyl)-amino]-3-methoxy-phenyl-acetic acid

A mixture of methyl 4-[(2,3-dihydro-indole-1-carbonyl)-amino]-3-methoxy-phenyl-acetate (5.2 g, Reference Example 6) and sodium hydroxide (20 mL, 1M) in methanol (100 mL) and water (50 mL) was stirred at 50° C. for 4 hours. The mixture was evaporated to low bulk and the aqueous layer was washed with dichloromethane then acidified with hydrochloric acid (1M) to give a tan precipitate. This material was filtered, washed with water, then with ether and then dried to give the title compound (4.3 g) as an off-white solid. HPLC: $R_T$=13.3 minutes (99% by ELS).

REFERENCE EXAMPLE 6

Methyl 4-[(2,3-dihydro-indole-1-carbonyl)-amino]-3-methoxy-phenyl-acetate

A stirred solution of methyl 4-amino-3-methoxyphenyl acetate (4.0 g) and triethylamine (2.9 mL) in dichloromethane (150 mL), cooled in an ice bath, was treated dropwise with a solution of trichloromethyl chloroformate (2.5 mL) in dichloromethane (30 mL), keeping the temperature of the mixture at 0 to 5° C. The ice bath was removed and the mixture was then stirred at room temperature for 2 hours. The mixture was washed with water (20 mL), then dried and then evaporated. The residue was dissolved in dichloromethane (100 mL) and the solution was treated with indoline (2.3 mL). After stirring at room temperature overnight this mixture was washed with water (100 mL), then with hydrochloric acid (1M), then dried and then evaporated to give the title compound (5.2 g) as a tan coloured powder. HPLC: $R_T$=17.3 minutes (87% by UV @ 200 nM).

In Vitro and In Vivo Test Procedures

1. Inhibitory Effects of Compounds on VLA-4 Dependent Cell Adhesion to Fibronectin and VCAM.

1.1 Metabolic Labelling of RAMOS Cells.

RAMOS cells (a pre-B cell line from ECACC, Porton Down, UK) are cultured in RPMI culture medium (Gibco, UK) supplemented with 5% foetal calf serum (FCS, Gibco, UK). Prior to assay the cells are suspended at a concentration of $0.5 \times 10^6$ cells/ml RPMI and labelled with 400 μCi/ 100 mls of [$^3$H]-methionine (Amersham, UK) for 18 hours at 37° C.

1.2 96 Well Plate Preparation for Adhesion Assay.

Cytostar plates (Amersham, UK) were coated with 50 μl/well of either 3 μg/ml human soluble VCAM-1 (R&D Systems Ltd, UK) or 28.8 μg/ml human tissue Fibronectin (Sigma, UK). In control non-specific binding wells 50 μl phosphate buffered saline was added. The plates were then left to dry in an incubator at 25° C., overnight. The next day the plates were blocked with 200 μl/well of Pucks buffer (Gibco, UK) supplemented with 1% BSA (Sigma, UK). The plates were left at room temperature in the dark for 2 hours. The blocking buffer was then disposed of and the plates dried by inverting the plate and gently tapping it on a paper tissue. 50 μl/well of 3.6% dimethyl sulphoxide in Pucks buffer supplemented with 5 mM manganese chloride (to activate the integrin receptor Sigma, UK) and 0.2% BSA (Sigma, UK), was added to the appropriate control test binding and non-specific binding assay wells in the plate. 50 μl/well of the test compounds at the appropriate concentrations diluted in 3.6% dimethyl sulphoxide in Pucks buffer supplemented with 5 mM manganese chloride and 0.2% BSA, was added to the test wells.

Metabolically labelled cells were suspended at $4 \times 10^6$ cells/ml in Pucks buffer that was supplemented with manganese chloride and BSA as above. 50 μl/well of cells in 3.6% dimethyl sulphoxide in Pucks buffer and supplements was added to all plate wells. The same procedure exists for plates coated with either VCAM-1 or fibronectin and data is determined for compound inhibition of cell binding to both substrates.

1.3 Performance of Assay and Data Analysis.

The plates containing cells in control or compound test wells are incubated in the dark at room temperature for 1 hour.

The plates are then counted on a Wallac Microbeta scintillation counter (Wallac, UK) and the captured data processed in Microsoft Excel (Microsoft, US). The data was expressed as an IC50, namely the concentration of inhibitor at which 50% of control binding occurs. The percentage binding is determined from the equation:

$$\{[(C_{TB}-C_{NS})-(C_I-C_{NS})]/(C_{TB}-C_{NS})\} \times 100 = \% \text{ binding}$$

where $C_{TB}$ are the counts bound to fibronectin (or VCAM-1) coated wells without inhibitor present, $C_{NS}$ are the counts present in wells without substrate, and $C_I$ are the counts present in wells containing a cell adhesion inhibitor.

Compound data of this invention is expressed for $IC_{50}$s for inhibition of cell adhesion to both fibronectin and VCAM-1. Particular compounds of the invention inhibit cell adhesion to fibronectin and VCAM-1 with $IC_{50}$s in the range 100 micromolar to 1 nanomolar. Preferred compounds of the invention inhibit cell adhesion to fibronectin and VCAM-1 with $IC_5sOS$ in the range 10 nanomolar to 1 nanomolar.

2. Inhibition of Antizen-induced Airway Inflammation in the Mouse and Rat.

2.1 Sensitization of the Animals.

Rats (Brown Norway, Harland Olac, UK) are sensitized on days 0, 12 and 21 with ovalbumin (100 μg, intraperitoneally [i.p], Sigma, UK) administered with aluminium hydroxide adjuvant (100 mg, i.p., Sigma, UK) in saline (1 ml, i.p.).

In addition mice (C57) are sensitized on days 0 and 12 with ovalbumin (10 μg, i.p.) administered with aluminium hydroxide adjuvant (20 mg, i.p.) in saline (0.2 ml, i.p.).

2.2 Antigen Challenge.

Rats are challenged on any one day between days 28–38, while mice are challenged on any one day between days 20–30.

The animals are challenged by exposure for 30 minutes (rats) or 1 hour (mice) to an aerosol of ovalbumin (10 g/l) generated by an ultrasonic nebulizer (deVilbiss Ultraneb, US) and passed into an exposure chamber.

2.3 Treatment Protocols.

Animals are treated as required before or after antigen challenge. The aqueous-soluble compounds of this invention can be prepared in water (for oral, p.o. dosing) or saline (for intratracheal, i.t. dosing). Non-soluble compounds are prepared as suspensions by grinding and sonicating the solid in 0.5% methyl cellulose/0.2% polysorbate 80 in water (for p.o. dosing, both Merck UK Ltd., UK) or saline (for i.t. dosing). Dose volumes are: for rats 1 ml/kg, p.o. or 0.5 mg/kg, i.t.; for mice 10 ml/kg, p.o. or 1 ml/kg, i.t.

2.4 Assessment of Airway Inflammation.

The cell accumulation in the lung is assessed 24 hours after challenge (rats) or 48–72 hours after challenge (mice). The animals are euthanized with sodium pentobarbitone (200 mg/kg, i.p., Pasteur Merieux, France) and the trachea is immediately cannulated. Cells are recovered from the airway lumen by bronchoalveolar lavage (BAL) and from the lung tissue by enzymatic (collagenase, Sigma, UK) disaggregation as follows.

BAL is performed by flushing the airways with 2 aliquots (each 10 ml/kg) RPMI 1640 medium (Gibco, UK) containing 10% fetal calf serum (FCS, Serotec Ltd., UK). The recovered BAL aliquots are pooled and cell counts made as described below.

Immediately after BAL, the lung vasculature is flushed with RPMI 1640/FCS to remove the blood pool of cells. The lung lobes are removed and cut into 0.5 mm pieces. Samples (rats: 400 mg; mice: 150 mg) of homogenous lung tissue are incubated in RPMI 1640/FCS with collagenase (20 U/ml for 2 hours, then 60 U/ml for 1 hour, 37° C.) to disaggregate cells from the tissue. Recovered cells are washed in RPMI 1640/FCS.

Counts of total leukocytes recovered from the airway lumen and the lung tissue are made with an automated cell counter (Cobas Argos, US). Differential counts of eosinophils, neutrophils and mononuclear cells are made by light microscopy of cytocentrifuge preparations stained with Wright-Giemza stain (Sigma, UK). T cells are counted by flow cytometry (EPICS XL, Coulter Electronics, US) using fluophore-labelled antibodies against CD2 (a pan-T cell marker used to quantify total T cells), CD4, CD8 and CD25 (a marker of activated T cells). All antibodies were supplied by Serotec Ltd., UK)

2.5 Data Analysis.

The cell data was expressed as mean cell numbers in unchallenged, challenged and vehicle treated, and challenged and compound treated groups, including the standard error of the means. Statistical analysis of the difference among treatment groups was evaluated using one-way analysis of variance via the Mann-Whitney test. Where $p<0.05$ no statistical significance existed.

What is claimed is:

1. A compound of general formula (I):

$$\begin{array}{c} R^1 \quad O \\ \diagdown \quad \| \\ N-C-N-Ar^1-L^1-Ar^2-L^2-Y \\ | \quad \quad H \\ R^2 \end{array}$$ (I)

wherein:

$R^1$ and $R^2$ together with the nitrogen atom to which they are attached form a cyclic amine;

$R^3$ represents optionally substituted alkyl, alkenyl, alkynyl, aryl, arylalkyl, arylalkenyl, arylalkynyl, cycloalkyl, cycloalkylalkyl, cycloalkenyl, cycloalkenylalkyl, heteroaryl, heteroarylalkyl, heteroarylalkenyl, heteroarylalkynyl, heterocycloalkyl or heterocycloalkylalkyl;

$R^4$ represents hydrogen or optionally substituted lower alkyl;

$R^5$ is a straight or branched alkylene chain, alkenylene chain or alkynylene chain;

$R^6$ is cycloalkylene, heterocycloalkylene, aryldiyl, heteroaryldyl, $—C(=Z^1)—NR^4—$, $—NR^4—C(=Z^1)—$, $—Z^1—$, $—C(=O)—$, $—C(=NOR^4)—$, $—NR^4—$, $—NR^4—C(=Z^1)—NR^4—$, $—SO_2—NR^4—$, $—NR^4—SO_2—$, $—O—C(=O)—$, $—C(=O)—O—$, $—NR^4—C(=O)—O—$ or $—O—C(=O)—NR^4—$;

$R^7$ is hydrogen; or optionally substituted alkyl, aryl, arylalkyl, cycloalkyl, cycloalkylalkyl, heteroaryl, heteroarylalkyl, heterocycloalkyl or heterocycloalkylalkyl;

$R^8$ is optionally substituted alkyl, aryl, cycloalkyl, heteroaryl or heterocycloalkyl, or alkyl substituted by optionally substituted aryl, an acidic functional group, cycloalkyl, heteroaryl, heterocycloalkyl, $—Z^1H$, $—Z^2R^3$, $—C(=O)—NY^1Y^2$ or $—NY^1Y^2$;

$R^9$ is hydrogen, $R^3$ or alkyl substituted with alkoxy, cycloalkyl, hydroxy, mercapto, alkylthio or $—NY^1Y^2$;

$R^{10}$ is hydrogen or a group consisting amino acid side chains, an acidic functional group, $R^3$, $—Z^2R^3$, $—C(=O)—R^3$, or $—C(=O)—NY^1Y^2$, or alkyl substituted by an acidic functional group or by $R^3$, $—Z^2R^3$, $—NY^1Y^2$, $—NH—(=O)—R^3$, $—C(=O)—R^5—NH_2$, $—C(=O)—Ar^3—NH_2$, $—C(=O)—R^5—CO_2H$, or $—C(=O)—NY^1Y^2$;

or $R^9$ and $R^{10}$ together with the atoms to which they attached form a 3- to 6-membered heterocycloalkyl ring;

$R^{11}$ is $C_{1-6}$alkylene, optionally substituted by $R^3$;

$R^{12}$ is hydrogen, or alkyl optionally substituted by aryl, an acidic functional group, cycloalkyl, heteroaryl, heterocycloalkyl, $—Z^1H$, $—Z^2R^3$, $—C(=O)—NY^1Y^2$ or $—NY^1Y^2$;

$Ar^1$ is optionally substituted aryldiyl or heteroaryldiyl;

$Ar^2$ is heteroaryldiyl, phenylene or phenylene substituted by halogen, lower alkyl or lower alkoxy;

$Ar^3$ is aryldiyl or heteroaryldiyl;

$L^1$ represents a $—R^5—R^6—$ linkage;

$L^2$ represents:
  (i) a direct bond;
  (ii) an alkylene, alkenylene, alkynylene, cycloalkenylene, cycloalkylene, heteroaryldiyl, heterocycloalkylene or aryldiyl linkage each optionally substituted by (a) an acidic functional group, $R^3$, $—Z^1H$, $—Z^2R^8$, $—C(=O)—R^3$, $—N(R^7)—C(=O)—R^8$, $—N(R^7)—C(=O)—OR^8$, $—N(R^7)—C(=O)—NR^4R^8$, $—N(R^7)—SO_2—R^8$, $—NY^1Y^2$, or $—[C(=O)—N(R^9)—C(R^4)(R^{10})]_p—(=O)—NY^1Y^2$, or by (b) alkyl substituted by an acidic functional group, or by $—Z^1H$, $—Z^2R^3$, $—C(=O)—NY^1Y^2$ or $—NY^1Y^2$;
  (iii) a $—[C(=O)—N(R^9)—C(R^4)(R^{10})]_9—$ linkage;
  (iv) a $—Z^3—R^{11}—$ linkage;
  (v) a $—C(=O)—CH_2—C(=O)—$ linkage; or
  (vi) a $—R^{11}—Z^3—R^{11}—$ linkage;

Y is carboxy;

$Y^1$ and $Y^2$ are independently hydrogen; or optionally substituted alkenyl, alkyl, alkynyl, aryl, cycloalkenyl, cycloalkyl, heteroaryl, heterocycloalkyl, or alkyl substituted by alkoxy, aryl, cyano, cycloalkyl, heteroaryl, heterocycloalkyl, hydroxy, oxo, —$NY^3Y^4$, or one or more —$CO_2R^7$ or —C(=O)—$NY^3Y^4$ groups; or the group —$NY^1Y^2$ may form a cyclic amine;

$Y^3$ and $Y^4$ are independently hydrogen; or optionally substituted alkenyl, alkyl, aryl, arylalkyl, cycloalkyl, heteroaryl or heteroarylalkyl; or the group —$NY^3Y^4$ may form a cyclic amine;

$Z^1$ is O or S;

$Z^2$ is O or $S(O)_n$;

$Z^3$ is O, $S(O)_n$, $NR^{12}$, $SO_2NR^{12}$, $NR^{12}C(=O)$, $C(=O)NR^{12}$ or C(=O); and n is zero or an integer 1 or 2;

p is zero or an integer 1 to 4;

and the corresponding N-oxides, and their prodrugs; and pharmaceutically acceptable salts and solvates of such compounds and their N-oxides and prodrugs; but excluding compounds where an oxygen, nitrogen or sulphur atom is attached directly to a carbon carbon multiple bond of an alkenyl or alkynyl residue.

2. A compound according to claim 1 in which $R^1$ and $R^2$ together with the nitrogen atom to which they are attached form a bicyclic ring system consisting of a cyclic amine containing a 5–7 membered monocyclic cycloalkyl group wherein one of the ring carbon atoms is replaced by a nitrogen atom which is fused via ring carbon atoms to an aryl ring.

3. A compound according to claim 2 in which the fused aryl ring is optionally substituted phenyl.

4. A compound according to claim 1 in which $R^1$ and $R^2$ together with the nitrogen atom to which they are attached form an indolinyl ring.

5. A compound according to claim 1 in which $Ar^1$ represents aryldiyl.

6. A compound according to claim 5 in which $Ar^1$ represents optionally substituted phenylene.

7. A compound according to claim 6 in which $Ar^1$ represents p-phenylene or p-phenylene substituted by $C_{1-4}$alkyl, $C_{1-4}$alkoxy, $C_{1-4}$alkylthio, $C_{1-4}$alkylsulphinyl or $C_{1-4}$alkylsulphonyl.

8. A compound according to claim 7 in which $Ar^1$ represents p-phenylene or p-phenylene substituted by $C_{1-4}$alkoxy.

9. A compound according to claim 7 or claim 8 in which the located in the 3 position.

10. A compound according to claim 1 in which $L^1$ represents a —$R^5$—$R^6$— linkage where $R^5$ is a straight or branched $C_{1-4}$alkylene chain and $R^6$ represents —C(=O)—NH—.

11. A compound according to claim 10 in which $L^1$ represents —$CH_2$C(=O)—NH—.

12. A compound according to claim 1 in which $Ar^2$ represents optionally substituted p-phenylene.

13. A compound according to claim 12 in which $Ar^2$ represents unsubstituted p-phenylene.

14. A compound according to claim 1 in which $L^2$ represents a $C_{1-4}$alkylene linkage optionally substituted by $C_{1-4}$alkyl, aryl, heteroaryl, —$Z^2R^8$, —$N(R^7)$—C(=O)—$R^8$, —$N(R^7)$—C(=O)—$OR^8$, —$N(R^7)$—$SO_2$—$R^8$, —$NY^1Y^2$, —[C(=O)—$N(R^9)$—$C(R^4)(R^{10})]_p$—C(=O)—$NY^1Y^2$ or alkyl substituted by hydroxy, —$OR^3$, —C(=O)—$OR^7$ or —$NY^1Y^2$.

15. A compound according to claim 14 in which $L^2$ represents ethylene optionally substituted by $C_{1-4}$alkyl, aryl, heteroaryl, —$Z^2R^8$, —$N(R^7)$—C(=O)—$R^8$, —$N(R^7)$—C(=O)—$OR^8$, —$N(R^7)$—$SO_2$—$R^8$, —$NY^1Y^2$, —[C(=O)—$N(R^9)$—$C(R^4)(R^{10})]_p$—C(=O)—$NY^1Y^2$ or alkyl substituted by hydroxy, —$OR^3$, —C(=O)—$OR^7$ or —$NY^1Y^2$.

16. A compound according to claim 15 in which $L^2$ is a group $$-\underset{\underset{R^{14}}{|}}{\overset{\overset{R^{15}}{|}}{C}}-CH_2-,$$

where $R^{15}$ is hydrogen or $C_{1-4}$alkyl and $R^{14}$ represents $C_{1-4}$alkyl, or where $R^{15}$ is hydrogen and $R^{14}$ represents aryl, heteroaryl, —$Z^2R^8$, —$N(R^7)$—C(=O)—$R^8$, —$N(R^7)$—C(=O)—$OR^8$, —$N(R^7)$—$SO_2$—$R^8$, —$NY^1Y^2$, —[C(=O)—$N(R^9)$—$C(R^4)(R^{10})]_p$—C(=O)—$NY^1Y^2$ or alkyl substituted by hydroxy, —$OR^3$, —C(=O)—$OR^7$ or —$NY^1Y^2$.

17. A compound according to claim 16 in which $L^2$ is a group $$-\underset{\underset{R^{14}}{|}}{C}-CH_2-,$$

where $R^{14}$ represents $C_{1-4}$alkyl, —$Z^2R^8$, —$N(R^7)$—C(=O)—$R^8$, —$N(R^7)$—C(=O)—$OR^8$, —$N(R^7)$—$SO_2$—$R^8$, —$NY^1Y^2$, or alkyl substituted by hydroxy, —$OR^3$, —C(=O)—$OR^7$ or —$NY^1Y^2$.

18. A compound according to claim 17 in which $R^{14}$ represents —$N(R^7)$—C(=O)—$R^8$, —$N(R^7)$—C(=O)—$OR^8$, —$N(R^7)$—$SO_2$—$R^8$ or —$NY^1Y^2$.

19. A compound according to claim 17 in which $R^{14}$ represents —$N(R^7)$—(=O)—$R^8$.

20. A compound according to claim 1 of formula (Ia):

(Ia)

in which $Ar^1$, $Ar^2$, $L^2$ and Y are as defined in claim 1, and their prodrugs, and pharmaceutically acceptable salts and solvates of compounds of formula (Ia) and their prodrugs.

21. A pharmaceutical composition comprising an effective amount of a compound according to claim 1 or a corresponding N-oxide or prodrug, or a pharmaceutically acceptable salt or solvate of such a compound or an N-oxide prodrug thereof, in association with a pharmaceutically acceptable carrier or excipient.

22. A method for the treatment of a human or non-human animal patient suffering from, or subject to, a condition which can be ameliorated by the administration of an inhibitor of α4β1 mediated cell adhesion comprising administering to said patient an effective amount of a compound according to claim 1 or a corresponding N-oxide or prodrug, or a pharmaceutically acceptable salt or solvate of such a compound or an N-oxide or prodrug thereof.

23. A method for the treatment of a patient suffering from, or subject to, asthma comprising administering to said patient an effective amount of a compound according to claim 1 or a corresponding N-oxide or prodrug, or a pharmaceutically acceptable salt or solvate of such a compound or an N-oxide or prodrug thereof.

24. A method for the treatment of a patient suffering from, or subject to, an inflammatory disease comprising administering to said patient an effective amount of a compound according to claim 1 or a corresponding N-oxide or prodrug, or a pharmaceutically acceptable salt or solvate of such a compound or an N-oxide or prodrug thereof.

25. A method for the treatment of a human or non-human animal patient suffering from, or subject to, a condition which can be ameliorated by the administration of an inhibitor of $\alpha 4\beta 1$ mediated cell adhesion comprising administering to said patient an effective amount of a composition according to claim 21.

26. A method for the treatment of a patient suffering from, or subject to, asthma comprising administering to said patient an effective amount of a composition according to claim 21.

27. A method for the treatment of a patient suffering from, or subject to, an inflammatory disease comprising administering to said patient an effective amount of a composition according to claim 21.

* * * * *